US008859755B2

(12) United States Patent
Wada et al.

(10) Patent No.: US 8,859,755 B2
(45) Date of Patent: Oct. 14, 2014

(54) METHOD FOR PREPARING RIBONUCLEOSIDE PHOSPHOROTHIOATE

(75) Inventors: Takeshi Wada, Chiba (JP); Yohei Nukaga, Chiba (JP)

(73) Assignee: Chiralgen, Ltd., Kagoshima (JP)

( * ) Notice: Subject to any disclaimer, the term of this patent is extended or adjusted under 35 U.S.C. 154(b) by 258 days.

(21) Appl. No.: 13/582,531

(22) PCT Filed: Mar. 4, 2011

(86) PCT No.: PCT/JP2011/055018
§ 371 (c)(1),
(2), (4) Date: Apr. 4, 2013

(87) PCT Pub. No.: WO2011/108682
PCT Pub. Date: Sep. 9, 2011

(65) Prior Publication Data
US 2013/0184450 A1 Jul. 18, 2013

(30) Foreign Application Priority Data

Mar. 5, 2010 (JP) .................................. 2010-048824

(51) Int. Cl.
C07H 21/00 (2006.01)
C07H 19/10 (2006.01)
C07H 21/02 (2006.01)
C07H 19/20 (2006.01)
C07H 19/06 (2006.01)
C07H 19/16 (2006.01)

(52) U.S. Cl.
CPC ............... *C07H 19/20* (2013.01); *C07H 19/10* (2013.01); *C07H 21/02* (2013.01); *C07H 19/06* (2013.01); *C07H 19/16* (2013.01)
USPC ...................................... 536/25.33; 536/25.3

(58) Field of Classification Search
None
See application file for complete search history.

(56) References Cited

U.S. PATENT DOCUMENTS

2007/0282097 A1   12/2007   Ohgi et al.

FOREIGN PATENT DOCUMENTS

| CN | 1345328 A | 4/2002 |
|---|---|---|
| JP | 2009-190983 | 8/2009 |
| WO | 2005/092909 | 10/2005 |
| WO | 2006/022323 | 3/2006 |

OTHER PUBLICATIONS

Parrish et al., "Functional Anatomy of a dsRNA Trigger: Differential Requirement for the Two Trigger Strands in RNA Interference", Molecular Cell, vol. 6, 2000, pp. 1077-1087.
Braasch et al., "RNA Interference in Mammalian Cells by Chemically-Modified RNA", Biochemistry, vol. 42, No. 26, 2003, pp. 7967-7975.
Amarzguioui et al., "Tolerance for mutations and chemical modifications in a siRNA", Nucleic Acids Research, vol. 31, No. 2, 2003, pp. 589-595.
Burgers et al., "Absolute configuration of the diastereomers of adenosine 5'-O-(1-thiotriphosphate): Consequences for the stereochemistry of polymerization by DNA-dependent RNA polymerase from *Escherichia coli*", Proceedings of the National Academy of Sciences of the United States of America, vol. 75, No. 10, 1978, pp. 4798-4800.
Potter et al., "Synthesis and Configurational Analysis of a Dinucleoside Phosphate Isotopically Chiral at Phosphorus. Stereochemical Course of *Penicillium citrum* Nuclease P1 Reaction", Biochemistry, vol. 22, No. 6, 1983, pp. 1369-1377.
Potter et al., "Stereospecificity of nucleases towards phosphorothioate-substituted RNA: stereochemistry of transcription by T7 RNA polymerase", Nucleic Acids Research, vol. 15, No. 10, 1987, pp. 4145-4162.
Stawinski et al. "Synthesis of Diribonucleoside Phosphorothioates via Stereospecific Sulfurization of H-Phosphonate Diesters", Journal of Organic Chemistry, vol. 57, Issue 23, 1992, pp. 6163-6169.
Almer et al., "Solid support synthesis of all-*R*p-oligo(ribonucleoside phosphorothioate)s", Nucleic Acids Research, vol. 24, No. 19, 1996, pp. 3811-3820.
Sierzchala et al., "Oxathiaphospholane Method of Stereocontrolled Synthesis of Diribonucleoside 3',5'-Phosphorothioates", Journal of Organic Chemistry, vol. 61, Issue 19, 1996, pp. 6713-6716.
Oka et al., "Solid-Phase Synthesis of Stereoregular Oligodeoxyribonucleoside Phosphorothioates using Bicyclic Oxazaphospholidine Derivatives as Monomer Unites", Journal of American Chemical Society, vol. 130, 2008, pp. 16031-16037.
Welz et al., "5-(Benzylmercapto)-1*H*-tetrazole as activator for 2'-O-TBDMS phosphoramidite building blocks in RNA synthesis", Tetrahedron Letters, vol. 43, 2002, pp. 795-797.
International Preliminary Report on Patentability and Written Opinion of the Searching Authority for PCT/JP2011/055018, dated Oct. 11, 2012 with English Translation thereof.
Office Action issued with respect to Chinese Application No. 201180012325.6, mail date is Mar. 11, 2014.
MaoJun Guo et al., "Solid-Phase Stereoselective Synthesis of 2'-O-Methyl-Oligoribonucleoside Phosphorothioates Using Neucleoside Bicyclic Oxazaphospholidines", Bioorganic & Medicinal Chemistry Letters 8 (18), 1998, pp. 2539-2544.
Natsuhisa Oka et al., "Stereocontrolled Synthesis of Oligoribonucleoside Phosphorothioates by an Oxazaphospholidine Approach", Organic Letters, 2009, pp. 967-970.
Tadaaki Ohgi et al., "A New RNA Synthetic Method with a 2'-O-(2-Cyanoethoxymethyl) Protecting Group", Organic Letters, 2005, pp. 3477-3480.
Search report from International Application No. PCT/JP2011/055018, mail date is Mar. 29, 2011.

*Primary Examiner* — Patrick Lewis
(74) *Attorney, Agent, or Firm* — Greenblum & Bernstein, P.L.C.

(57) ABSTRACT

A method for preparing a phosphorothioate RNA based on the oxazaphospholidine method, wherein cyanoethoxymethyl group is used instead of tert-butyldimethylsilyl group as a protective group of 2'-hydroxyl group of RNA.

12 Claims, 3 Drawing Sheets

METHOD FOR PREPARING RIBONUCLEOSIDE PHOSPHOROTHIOATE

TECHNICAL FIELD

The present invention relates to a method for stereoselectively preparing a ribonucleoside phosphorothioate.

BACKGROUND ART

Phosphorothioate RNAs are RNA analogues in which one of non-crosslinked oxygen atoms in the phosphodiester bond is replaced with a sulfur atom. Since phosphorothioate RNAs are expected to have higher nuclease resistance and cell membrane permeability compared with naturally occurring RNAs, they are considered to be most promising RNA-type nucleic acid medicaments at present (Mol. Cell., 6, pp. 1077-1087, 2000; Biochemistry, 42, pp. 7967-7975, 2003; Nucleic Acids Res., 31, pp. 589-595, 2003, and the like).

Phosphorothioate RNAs have a chiral center at a phosphorus atom, thereby two kinds of stereoisomers (Rp- and Sp-isomers) exist. It is known that these stereoisomers have different biochemical and physical properties (Proc. Natl. Acad. Sci. USA, 75, pp. 4798-4800, 1978; Biochemistry, 22, pp. 1369-1377, 1983). Therefore, when a phosphorothioate RNA is prepared, it is desired to selectively prepare a compound having a desired stereochemical configuration. However, it is difficult to prepare a phosphorothioate RNA under control of the steric configuration on the phosphorus atom, and accordingly, it has been desired to provide a method that can achieve efficient stereoselective synthesis.

As synthetic methods for phosphorothioate RNAs, there are known the enzymatic method (Nucleic Acids Res., 10, pp. 4145-4162, 1987), the H-phosphonate method (J. Org. Chem., 57, pp. 6163-6169, 1992), the H-phosphonate method combined with an enzymatic reaction (Nucleic Acids Res., 24, pp. 3811-3820, 1996), and the oxathiaphosphorane method (J. Org. Chem., 61, pp. 6713-6716, 1996). However, any of these methods are considered to be unsatisfactory from a viewpoint of stereoselectivity and the like.

As a method for synthesizing a phosphorothioate DNA, there is known the method in which an optically pure nucleoside 3'-oxazaphospholidine derivative derived from an optically active 1,2-amino alcohol as a monomer unit is coupled by using a weakly acidic activator having low nucleophilicity, N-(cyanomethyl)pyrrolidinium triflate (CMPT) (oxazaphospholidine method, J. Am. Chem. Soc., 130, pp. 16031-16037, 2008). In this method, use of bicyclic oxazaphospholidine provides marked difference in the activation energy between the diastereomers in the nucleophilic substitution reaction on a phosphorus atom, and thus high diastereoselectivity is attained.

Further, this method also comprises steps of condensing the monomer unit to the nucleoside derivative immobilized on the solid phase carrier such as controlled pore glass (CPG), and then capping unreacted 5'-hydroxyl group and the secondary amine of the asymmetric auxiliary group, followed by sulfurizing the phosphite, and removing 4,4'-dimethoxytrityl (DMTr) group at the 5'-end as deprotection. By repeating the steps according to an objective nucleotide sequence, a long chain phosphorothioate DNA can be synthesized. In the aforementioned publication, synthesis of a stereochemically pure thymidyl phosphorothioate decamer is reported.

There has been reported a method for stereoselectively synthesizing a phosphorothioate by applying the aforementioned oxazaphospholidine method to the synthesis of phosphorothioate RNA (Org. Lett., 11, pp. 967-970, 2009). By this method, a tetramer or higher oligomer was successfully synthesized by using tert-butyldimethylsilyl (TBDMS) group as a protective group of 2'-hydroxyl group of RNA, which is stable under the chain extension reaction conditions and can be easily removed with tetrabutylammonium fluoride (TBAF) under a neutral condition for deprotection, and by using CMPT as an activator. All-(Rp)-[Ups]$_9$U and all-(Sp)-[Ups]$_9$U are stereoselectively synthesized.

However, this method has problems of low reactivity and insufficient condensing efficiency for synthesis of a long chain oligomer. According to the researches by the inventors of the present invention, the condensing efficiency can be improved by using benzimidazolium triflate (BIT) or N-phenylimidazolium triflate (PhIMT) having nucleophilicity higher than that of CMPT as an activator, and uridyl phosphorothioate decamer can be stereoselectively synthesized. However, the use of the highly nucleophilic activator causes another problem that epimerization advances to reduce the diastereoselectivity.

As a protective group for 2'-hydroxyl group used in preparation of nucleic acid derivatives such as oligoribonucleic acids, cyanoethoxymethyl group (—CH$_2$—O—CH$_2$—CH$_2$—CN, CEM) is known (Org. Lett., 7, pp. 3477-3480, 2005; International Patent Publication WO2006/22323). This protective group can be removed by reacting with fluorine ions under a neutral condition. An average condensing yield in coupling of monomers protected with TBDMS is 97% (Tetrahedron Letters, 43, pp. 795-797, 2002, page 795, left column, lines 8 to 11), whilst this protective group provides an average condensation yield of 99% or higher in a similar condensing reaction (Org. Lett., 7, pp. 3477-3480, 2005, page 3479, right column, lines 5 to 3 from the bottom). In the patent document disclosing the oxazaphospholidine method (WO2005/92909), 2-(cyanoethoxy)ethyl group (CEE) is exemplified as the protective group of the 2'-hydroxyl group. However, the document does not refer to cyanoethoxymethyl group.

PRIOR ART REFERENCES

Non-Patent Documents

Non-patent document 1: Mol. Cell., 6, pp. 1077-1087, 2000
Non-patent document 2: Biochemistry, 42, pp. 7967-7975, 2003
Non-patent document 3: Nucleic Acids Res., 31, pp. 589-595, 2003
Non-patent document 4: Proc. Natl. Acad. Sci. USA, 75, pp. 4798-4800, 1978
Non-patent document 5: Biochemistry, 22, pp. 1369-1377, 1983
Non-patent document 6: Nucleic Acids Res., 10, pp. 4145-4162, 1987
Non-patent document 7: J. Org. Chem., 57, pp. 6163-6169, 1992
Non-patent document 8: Nucleic Acids Res., 24, pp. 3811-3820, 1996
Non-patent document 9: J. Org. Chem., 61, pp. 6713-6716, 1996
Non-patent document 10: J. Am. Chem. Soc., 130, pp. 16031-16037, 2008
Non-patent document 11: Org. Lett., 11, pp. 967-970, 2009
Non-patent document 12: Tetrahedron Letters, 43, pp. 795-797, 2002
Non-patent document 13: Org. Lett., 7, pp. 3477-3480, 2005

Patent Documents

Patent document 1: International Patent Publication WO2006/22323
Patent document 2: WO2005/92909

SUMMARY OF THE INVENTION

Object to be Achieved by the Invention

An object of the present invention is to provide a method for stereoselectively and efficiently synthesizing an oligoribonucleoside phosphorothioate.

Means for Achieving the Object

The inventors of the present invention conducted various researches to improve the method for synthesizing a phosphorothioate RNA based on the oxazaphospholidine method described in Org. Lett., 11, pp. 967-970, 2009, and as a result, they found that when cyanoethoxymethyl group is used as the protective group of the 2'-hydroxyl group of RNA, instead of tert-butyldimethylsilyl group, an extremely high condensing efficiency was successfully attained, and that a high condensing efficiency satisfactorily applicable to synthesis of a long chain oligoribonucleoside phosphorothioate was also successfully obtained without degrading the diastereoselectivity, even when the weakly nucleophilic activator, N-(cyanomethyl)pyrrolidinium triflate, was used. Further, they also found that even when the highly nucleophilic activator, N-phenylimidazolium triflate (PhIMT) was used, high stereoselectivity was obtained, and high condensing efficiency sufficiently applicable to synthesis of a long chain oligoribonucleoside phosphorothioate containing four kinds of nucleobases was obtainable. The present invention was accomplished on the basis of the aforementioned findings.

The present invention thus provides a method for preparing a ribonucleoside phosphorothioate represented by the following general formula (I) or a salt thereof.

[Formula 1]

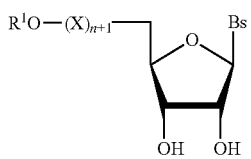

(I)

wherein, $R^1$ represents hydrogen atom or a protective group of hydroxyl group, Bs represents a nucleobase which may have a protective group, n represents 0 or an integer of 1 or larger, and n of X independently represent a divalent group represented by the following general formula (II-Sp) or (II-Rp):

[Formula 2]

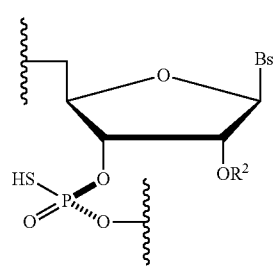

(II-Sp)

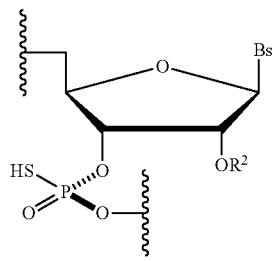

(II-Rp)

wherein, Bs has the same meaning as that defined above, and $R^2$ represents hydrogen atom or cyanoethoxymethyl group, which comprises the step of condensing a compound represented by the following general formula (III):

[Formula 3]

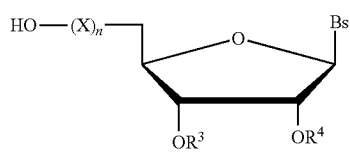

(III)

wherein, Bs, X, and n have the same meanings as those defined above, $R^3$ and $R^4$ independently represent a protective group of hydroxyl group, and one of $R^3$ and $R^4$ may optionally represents a solid phase carrier bound via a linker as required, with an oxazaphospholidine ribonucleoside represented by the following general formula (IVa) or (IVb):

[Formula 4]

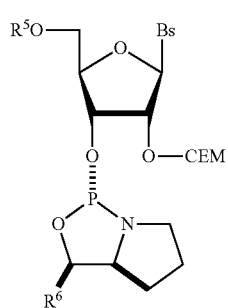

(IVa)

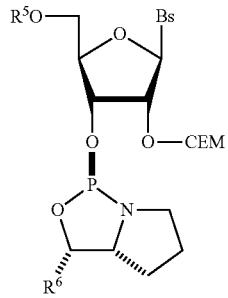

(IVb)

wherein, Bs has the same meaning as that defined above, CEM represents cyanoethoxymethyl group, $R^5$ represents a protective group of hydroxyl group, and $R^6$ represents an aryl group which may have a substituent, and then sulfurizing the resulting product.

According to preferred embodiments of the aforementioned method, there are provided the aforementioned method, wherein $R^6$ is phenyl group; the aforementioned method, wherein $R^5$ is 4,4'-dimethoxytrityl group; the aforementioned method, wherein the condensation is performed in the presence of an activator; the aforementioned method, wherein N-(cyanomethyl)pyrrolidinium triflate (CMPT) or N-phenylimidazolium triflate (PhIMT) is used as the activator; the aforementioned method, wherein dimethyl thiuram disulfide (DTD) is used as a sulfurizing agent; the aforementioned method, wherein the reaction is performed by a solid phase method; and the aforementioned method, wherein all of n+1 of X are divalent groups represented by the formula (II-Sp), or all of them are divalent groups represented by the formula (II-Rp).

From another aspect, the present invention provides a ribonucleoside phosphorothioate represented by the aforementioned general formula (I), wherein $R^1$, Bs, n, and X have the same meanings as those defined above, and $R^2$ represents cyanoethoxymethyl group, or a salt thereof.

Further, the present invention also provides an oxazaphospholidine ribonucleoside represented by the aforementioned general formula (IVa) or (IVb), wherein Bs, CEM, $R^5$, and $R^6$ have the same meanings as those defined above.

Effect of the Invention

By the method of the present invention, an oligoribonucleoside phosphorothioate can be stereoselectively and efficiently synthesized. According to the method of the present invention, extremely high stereoselective condensing efficiency can be attained, and therefore by applying the method as the solid phase method, a long chain oligoribonucleoside phosphorothioate can be prepared in a high yield.

MODES FOR CARRYING OUT THE INVENTION

Figure 1:
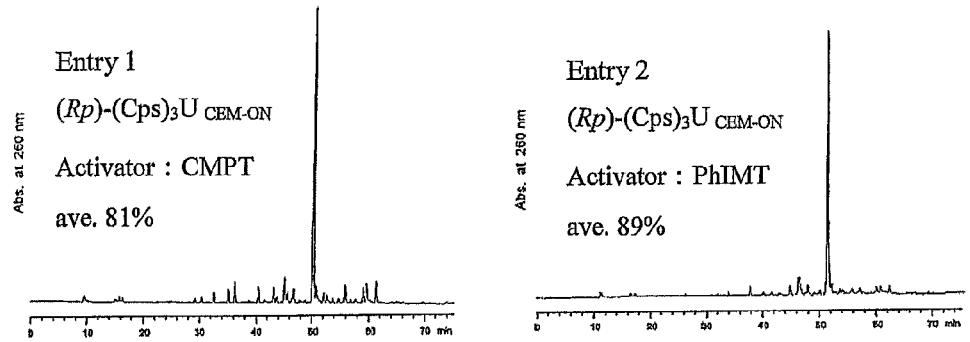
FIG. 1 shows the HPLC profiles of the phosphorothioate RNA tetramers obtained in Example 6.

In the general formula (I), $R^1$ represents hydrogen atom or a protective group of hydroxyl group. The type of the protective group of hydroxyl group is not particularly limited, and it is generally possible to use an appropriate protective group, for example, an acetyl protective group such as acetyl group and phenoxyacetyl group (Pac), a benzyl protective group such as benzyl group and 4-methoxybenzyl group, benzoyl group, pivaloyl group, a trityl protective group such as 4,4'-dimethoxytrityl group (DMTr), a silyl protective group such as trimethylsilyl group (TMS) and tert-butyldimethylsilyl group (TBDMS), an ether protective group such as 2-(cyanoethoxy)ethyl group (CEE) and cyanoethoxymethyl group (CEM), and the like. As for the protective group of hydroxyl group, published documents such as Green et al., Protective Groups in Organic Synthesis, 3rd Edition, 1999, John Wiley & Sons, Inc. can be referred to. When $R^1$ represents a protective group, the protective group of $R^1$ is preferably a protective group different from the other protective groups so that this protective group or the other protective groups can be selectively removed in the synthetic process. As the protective group of $R^1$, for example, a trityl protective group is preferably used, and 4,4'-dimethoxytrityl group is more preferably used.

Bs represents a nucleobase which may have a protective group. As the nucleobase, a nucleobase selected from the group consisting of adenine, uracil, thymine, guanine, and cytosine, as well as an arbitrary modified base such as ribothymidine and 5-methyluridine may be used. A nucleobase selected from the group consisting of adenine, uracil, guanine, and cytosine, which are constituent bases of RNA, can be preferably used. The nucleobase as a residue can be bound with a ribose at a usual bonding position. Bs in the other general formulas has the same meaning as that explained above.

When the nucleobase has a protective group, the type of the protective group is not particularly limited. When a nucleobase having amino group is used, the amino group can be protected. For example, it may be preferable to protect amino group of adenine, guanine, or cytosine, which is a nucleobase having amino group, and as the protective group, for example, benzoyl group, 4-methoxybenzoyl group, acetyl group, propionyl group, butyryl group, isobutyryl group, phenylacetyl group, phenoxyacetyl group, 4-tert-butylphenoxyacetyl group, 4-isopropylphenoxyacetyl group, (dimethylamino)methylene group, and the like can be used. The same shall apply to Bs in the other general formulas. N+2 of Bs in the ribonucleoside phosphorothioate represented by the general formula (I) or a salt thereof may be the same or different.

Symbol n represents 0 or an integer of 1 or larger, and is preferably an integer of 100 or smaller, more preferably an integer of 50 or smaller, still more preferably an integer of 40 or smaller. In the general formula (I), n of X independently represents a divalent group represented by the aforementioned general formula (II-Sp) or (II-Rp), and n of Bs contained in n of X may be the same or different as explained above. $R^2$ represents hydrogen atom or cyanoethoxymethyl group. The compounds wherein $R^2$ is hydrogen atom can be produced by preparing the ribonucleoside phosphorothioate wherein $R^2$ is cyanoethoxymethyl group according to the method for preparation of the present invention, and then removing the cyanoethoxymethyl group.

The type of the salt of the ribonucleoside phosphorothioate represented by the general formula (I) is not particularly limited. For example, ammonium salts and salts of organic amine, as well as metal salts, such as sodium salts, potassium salts, and magnesium salts, are preferred, and for example, ammonium salts, salts of a tertiary alkylamine compound such as triethylamine salts, sodium salts, and the like can be more preferably used. The ribonucleoside phosphorothioate represented by the general formula (I) or a salt thereof may be in the form of a hydrate or a solvate. The definition of the stereochemical configuration in the ribonucleoside phosphorothioate represented by the general formula (I) indicates absolute configuration. It is also possible to prepare an enantiomer of the ribonucleoside phosphorothioate represented by the general formula (I) according to the method of the present invention.

The ribonucleoside phosphorothioate represented by the general formula (I) can be prepared by condensing a compound represented by the aforementioned general formula (III) with an oxazaphospholidine ribonucleoside represented by the aforementioned general formula (IVa) or (IVb), followed by sulfurizing the resulting product. In the general formula (III), $R^3$ and $R^4$ independently represent a protective group of hydroxyl group. The protective group of hydroxyl group is the same as those explained above, and an appropriate protective group can be chosen depending on a purpose. The protective groups represented by $R^3$ and $R^4$ may be the same or different. Further, when the solid phase method is used, one of $R^3$ and $R^4$ may be a solid phase carrier bound via a linker, as required. In such a case, for the other group, a common protective group of hydroxyl group can be used.

The type of the solid phase carrier is not particularly limited, and an arbitrary solid phase carrier that can be used as a solid phase carrier in synthesis of a nucleic acid derivative can be used. The type and length of the linker are not particularly limited, and they can be appropriately chosen by those skilled in the art. Examples of the solid phase carrier include, for example, controlled pore glass (CPG), oxalylated controlled pore glass (Nucleic Acids Res., 19, 1527, 1991, and the like), TentaGel support-aminopolyethylene glycol derivatization support (Tetrahedron Letters, 34, 3373, 1993, and the like), copolymer of Poros-polystyrene/divinylbenzene, and the like. As particularly preferred solid phase carriers, highly cross-linked aminomethyl polystyrene (highly cross-linked polystyrene, HCP, Tetrahedron Letters, 32, 4096, 1991), and the like can be used. Examples of the linker include, for example, 3-aminopropyl group, succinyl group, 2,2'-diethanolsulfonyl group, a long chain alkylamino group (LCAA), and the like.

In the oxazaphospholidine ribonucleoside represented by the general formula (IVa) or (IVb), $R^5$ represents a protective group of hydroxyl group. The protective group of hydroxyl group is the same as those explained above, and an appropriate protective group can be chosen according to the object. For example, it is preferable to use a trityl protective group, and it is more preferable to use 4,4'-dimethoxytrityl group. $R^6$ represents an aryl group which may have a substituent. As the aryl group, a monocyclic or condensed polycyclic aryl group can be used, and phenyl group can be preferably used. The phenyl group may have one or more substituents, such as an alkyl group, an alkoxyl group, and a halogen atom. Unsubstituted phenyl group can be preferably used as $R^6$.

The aforementioned condensation reaction and the sulfurization reaction can be performed by referring to the conditions described in J. Am. Chem. Soc., 130, pp. 16031-16037, 2008; Org. Lett., 11, pp. 967-970, 2009; and WO2005/92909. The entire disclosure of the aforementioned patent document (WO2005/92909) is incorporated in the disclosure of the present specification by reference. In order to increase efficiency of the condensation reaction, the reaction can be performed in the presence of an activator. The type of the activator is not particularly limited. The method of the present invention provides extremely high reactivity, and accordingly, even when a weakly nucleophilic N-(cyanomethyl) pyrrolidinium triflate (CMPT) or the like is used for example, condensing efficiency can be markedly improved without degrading stereoselectivity. Further, with N-phenylimidazolium triflate (PhIMT), which is a highly nucleophilic activator, high stereoselectivity can also be attained, and high condensing efficiency sufficiently applicable to synthesis of a long chain oligoribonucleoside phosphorothioate containing four kinds of nucleobases can be achieved. The sulfurizing agent is not particularly limited. For example, dimethyl thiuram disulfide (DTD) and the like can be used.

In the aforementioned method, n+1 of X may consist of a combination of arbitrary numbers of divalent groups represented by the formulas (II-Sp) and (II-Rp). However, it is preferable to prepare a ribonucleoside phosphorothioate of the general formula (I), wherein all of n+1 of X are divalent groups represented by (II-Sp), or all of them are divalent groups represented by the formula (II-Rp).

After the ribonucleoside phosphorothioate represented by the general formula (I) is prepared by condensing a compound represented by the aforementioned general formula (III) with an oxazaphospholidine ribonucleoside represented by the aforementioned general formula (IVa) or (IVb), and then sulfurizing the product, the resulting ribonucleoside phosphorothioate can be used as a starting material, and condensed with an oxazaphospholidine ribonucleoside represented by the aforementioned general formula (IVa) or (IVb), and the product can be sulfurized to prepare a compound in which the number of the ribonucleoside phosphorothioate unit (X) is increased by one. Further, the compound obtained can be used as a starting material, and condensed with an oxazaphospholidine ribonucleoside represented by the aforementioned general formula (IVa) or (IVb), and the resulting product can be sulfurized to further increase the number of the ribonucleoside phosphorothioate units (X) in the compound by one. By repeating this reaction, a desired ribonucleoside phosphorothioate represented by the general formula (I) having n+1 of the ribonucleoside phosphorothioate units (X) can be prepared.

The preparation of the ribonucleoside phosphorothioate by repetition of the aforementioned reaction can be preferably performed by the solid phase method. The synthesis can also be performed with an automatic synthesizer by applying the solid phase oligonucleic acid synthesis method. As for the solid phase method, various references can be referred to, and those skilled in the art can easily choose appropriate conditions. For example, conditions of the capping and cleavage form the solid phase carrier used for carrying out the solid phase method can also be appropriately chosen by those skilled in the art.

The cyanoethoxymethyl group can be selectively removed for deprotection with tetrabutylammonium fluoride (TBAF) (Nucleic Acids Res., 35, pp. 3287-3296, 2007). In order to suppress addition of acrylonitrile by-produced in connection with the deprotection to the nucleobase, a small amount (for example, about 0.5%) of nitromethane can be added as a scavenger of acrylonitrile to suppress the side reaction and thereby perform the deprotection in a high yield.

EXAMPLES

Hereafter, the present invention will be still more specifically explained with reference to examples. However, the scope of the present invention is not limited by the following examples.

Example 1

(a) O$^6$-Cyanoethyl-N$^2$-phenoxyacetyl-3',5'-O-(di-tert-butylsilanediyl)-2'-O-(2-cyanoethoxymethyl)guanosine

[Formula 5]

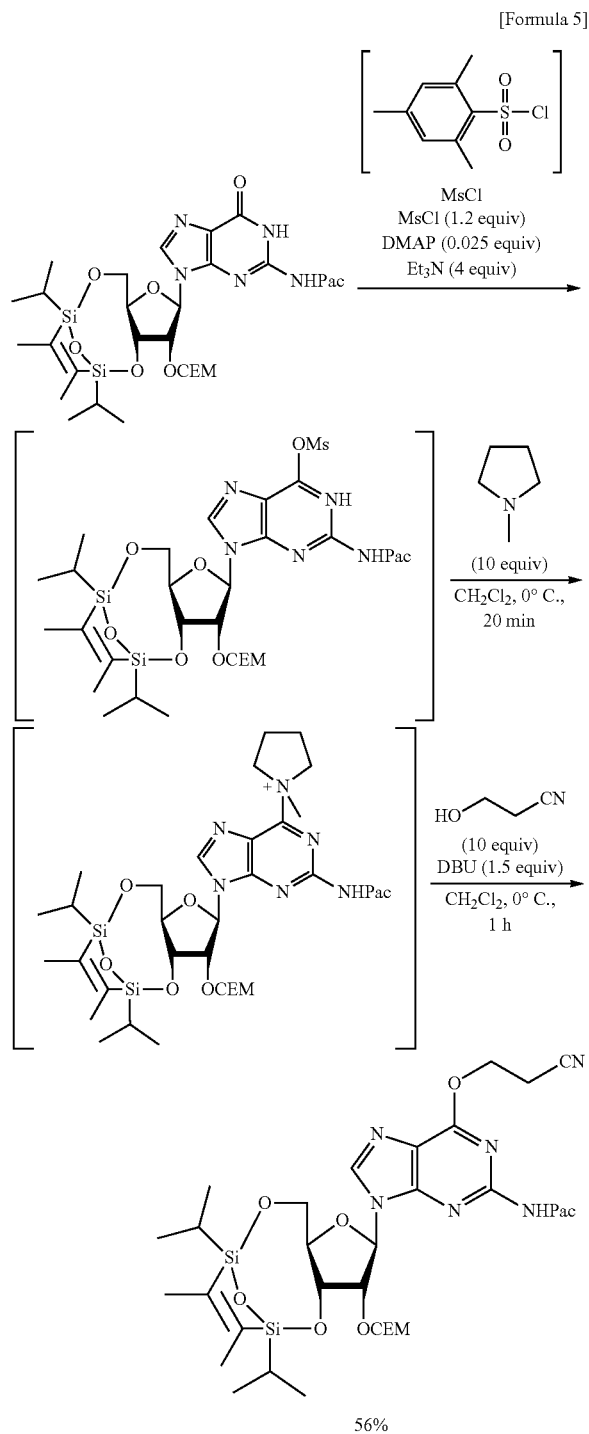

56%

N$^2$-Phenoxyacetyl-3',5'-O-(tetraisopropyldisiloxane-1,3-diyl)-2'-O-(2-cyanoethoxymethyl)guanosine (11.175 g, 14.9 mmol) was dried by repetition of azeotropy with toluene and dichloromethane to prepare a solution in dichloromethane (100 ml). N,N-Dimethylaminopyridine (DMAP, 0.092 g, 0.75 mmol), triethylamine (8.3 ml, 59.6 mmol) and mesitylenesulfonyl chloride (3.920 g, 17.9 mmol) were added to the solution, and the mixture was stirred at room temperature for 30 minutes. The reaction mixture was washed with saturated aqueous sodium hydrogencarbonate (30 ml×3), and the combined washing solution was extracted with dichloromethane (30 ml×2). The organic layer was dried over anhydrous sodium sulfate, then filtered, and concentrated under reduced pressure. The residue was dried by repetition of azeotropy with toluene and dichloromethane to obtain a solution in dichloromethane (100 ml). This solution was cooled to 0° C., and added with N-methylmorpholine (15.9 ml, 149 mmol), and the mixture was stirred at the same temperature, 0° C., for 20 minutes. This reaction mixture was added with 2-cyanoethanol (10.1 ml, 149 mmol), and 1,8-diazabicyclo[5,4,0]undec-7-ene (BDU, 3.3 ml, 22.1 mmol), and the mixture was stirred at 0° C. for 25 minutes, and then added with 1 M aqueous KH$_2$PO$_4$ (50 ml). The organic layer was separated, and washed with 1 M aqueous KH$_2$PO$_4$ (50 ml×2), and the combined washing solution was extracted with dichloromethane (30 ml×2). The organic layer was dried over anhydrous sodium sulfate, then filtered and concentrated under reduced pressure. The residue was purified by silica gel column chromatography [200 g of silica gel, ethyl acetate/hexane (50:50, v/v→100:0, v/v). The purified product was washed with saturated aqueous sodium hydrogencarbonate (30 ml×3), and the combined washing solution was extracted with dichloromethane (30 ml×2). The organic layer was dried over anhydrous sodium sulfate, then filtered and concentrated under reduced pressure to obtain the objective compound (6.200 g, 52%, colorless amorphous).

$^1$H NMR (300 MHz, CDCl$_3$) δ 8.92 (H, br.s, 2-NH), 8.31 (H, s, 8-H), 7.38-7.40 (2H, m, m of Pac), 6.98-7.11 (3H, m, o, p of Pac), 6.16 (H, s, 1'-H), 5.10, 5.20 (H, 2d, $^3$J=7.2 Hz, —OCH$_2$ of CEM), 4.77-4.85 (3H, m, 2'-H, —OCH$_2$ of Ce), 4.69 (2H, s, —CH$_2$ of Pac), 4.53 (H, dd, $^3$J=4.2, 9.3 Hz, 3'-H), 4.29-4.35 (2H, m, —OCH$_2$O of CEM), 4.01-4.08 (2H, m, 5'-H), 3.81-3.92 (H, m, 4'-H), 3.02 (2H, t, $^3$J=6.8 Hz, —CH$_2$CN of Ce), 2.61-2.66 (2H, m, —CH$_2$CN of CEM), 0.95-1.12 (32H, m, t-Bu)

(b) O$^6$-Cyanoethyl-N$^2$-phenoxyacetyl-2'-O-(2-cyanoethoxymethyl)guanosine

[Formula 6]

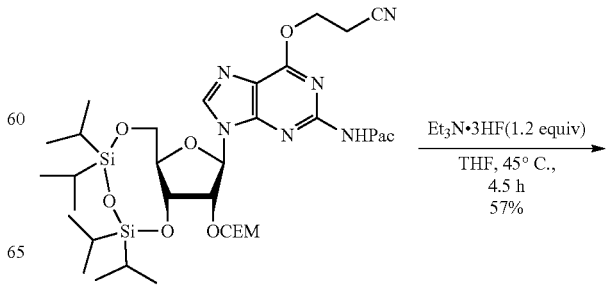

Et$_3$N·3HF (1.2 equiv)
THF, 45° C.,
4.5 h
57%

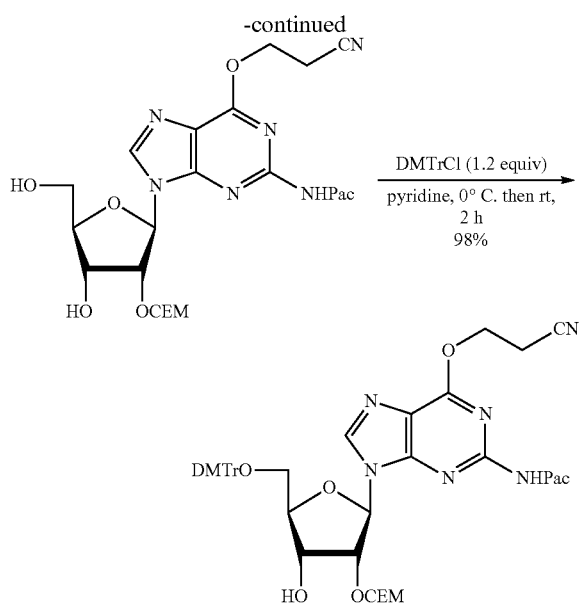

O⁶-Cyanoethyl-N²-phenoxyacetyl-3',5'-O-(di-tert-butyl-silanediyl)-2'-O-(2-cyanoethoxymethyl)guanosine (5.280 g, 6.6 mmol) was dried by repetition of azeotropy with toluene and tetrahydrofuran to obtain a solution in tetrahydrofuran (35 ml). This solution was heated to 35° C., and carefully added dropwise with triethylamine.3HF (1.3 ml, 8.0 mmol), and the mixture was stirred at the same temperature, 35° C., for 4.5 hours. The reaction mixture was cooled to 0° C., and then added with 5 ml of water, and the mixture was stirred at the same temperature, 0° C., for 1 hour. After tetrahydrofuran in the reaction mixture was evaporated under reduced pressure, the residue was added with diethyl ether (7.5 ml), and the mixture was stirred at room temperature for 1 hour. The produced precipitates were collected by suction filtration, and washed with diethyl ether (3 ml×3), and the solvent was evaporated under reduced pressure. The residue was recrystallized from methanol (40 ml), the resulting crystals were washed with diethyl ether (3 ml×3), and the solvent was evaporated under reduced pressure to obtain the objective compound (2.105 g, 57%, colorless amorphous).

¹H NMR (300 MHz, DMSO-d6) δ 8.57 (H, s, 8-H), 7.28-7.33 (2H, m, m of Pac), 6.93-6.96 (3H, m, o. p of Pac), 6.09 (H, d, ³J=6.0 Hz, 1'-H), 5.39-5.41 (H, m, 2'-H), 5.11 (2H, t, ³J=5.3 Hz, —CH₂ of Pac), 5.05 (H, br.s, 3'-OH), 4.67-4.78 (3H, m, 5'-OH, —OCH₂O of CEM), 4.36 (1H, ddd, ³J=3.6, 3.6, 4.7 Hz, 3'-H), 3.98 (H, d, ³J=3.6 Hz, 4'-H), 3.57-3.72 (3H, m, 5'-H, —OCH₂ of Ce), 3.32-3.48 (2H, m, —OCH₂ of CEM), 3.16-3.22 (2H, m, —CH₂CN of Ce), 2.50-2.66 (2H, m, —CH₂CN of CEM)

(c) O⁶-Cyanoethyl-N²-phenoxyacetyl-5'-O-(4,4'-dimethoxytrityl)-2'-O-(2-cyanoethoxymethyl)guanosine O⁶-Cyanoethyl-N²-phenoxyacetyl-2'-O-(2-cyanoethoxymethyl)guanosine (1.633 g, 3.0 mmol) was dried by repetition of azeotropy with pyridine to obtain a solution in the pyridine solvent (10 ml). This solution was cooled to 0° C., and added with 4,4'-dimethoxytrityl (DMTr) chloride (1.197 g, 3.5 mmol). The mixture was stirred for 2 hours while the temperature was increased to room temperature, and then added with methanol (5 ml), the solvent was evaporated under reduced pressure, and the residue was made into a solution in chloroform (50 ml). This solution was washed with saturated aqueous sodium hydrogencarbonate (30 ml×3), and the combined washing solution was extracted with chloroform (20 ml×3). The organic layer was dried over anhydrous sodium sulfate, then filtered, and concentrated under reduced pressure. The residue was purified by silica gel column chromatography [55 g of silica gel, ethyl acetate/hexane/pyridine (25:75:0.5, v/v/v→100:0:0.5, v/v/v) to obtain the objective substance (2.467 g, 98%, colorless amorphous).

¹H NMR (300 MHz, CDCl₃) δ 8.88 (H, s, 2-NH), 8.10 (H, s, 8-H), 6.99-7.42 (14H, m, Ph, m to OMe of DMTr, Ph of Pac), 6.79 (4H, d, ³J=8.1 Hz, o to OMe of DMTr), 6.24 (H, d, ³J=3.9 Hz, 1'-H), 5.01 (H, d, ³J=7.2 Hz, —OCH₂ of CEM), 4.95 (H, d, ³J=6.9 Hz, —OCH₂ of CEM), 4.79-4.90 (3H, m, 2'-H, —OCH₂ of Ce), 4.65 (2H, br.s, —CH₂ of Pac), 4.26 (H, d, ³J=3.3 Hz, 3'-H), 3.65-3.78 (9H, m, —OMe of DMTr, —OCH₂O of CEM, 4'-H), 3.49 (2H, s, 5'-H), 3.36 (H, br.s, 3'-OH), 3.02 (2H, t, ³J=6.6 Hz, —CH₂CN of Ce), 2.50 (2H, t, ³J=6.2 Hz, —CH₂CN of CEM)

Example 2

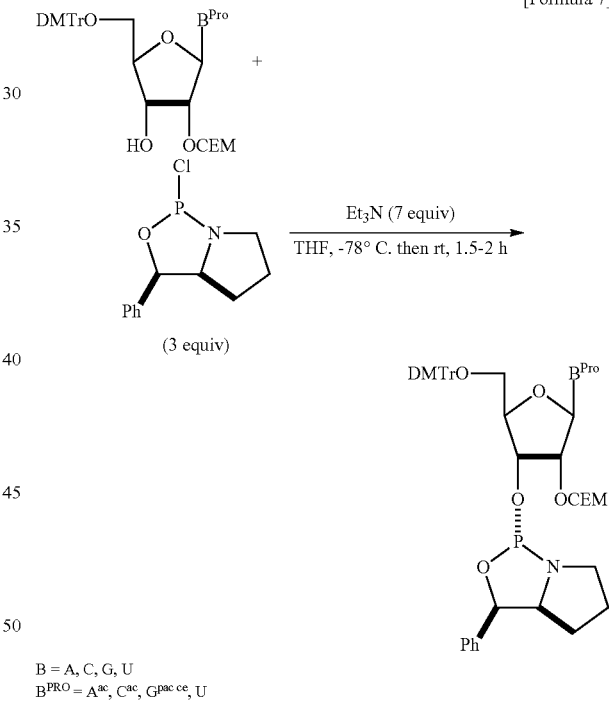

[Formula 7]

B = A, C, G, U
B^PRO = A^ac, C^ac, G^pac ce, U (a) 5'-O-(4,4'-Dimethoxytrityl)-3-O-[(2R,4S,5R)-5-phenyl-tetrahydro-1H,3H-pyrrolo[1,2-c]-1,3,2-oxazaphospholidin-2-yl]-2'-O-(2-cyanoethoxymethyl) uridine [(Rp)]

5'-O-(4,4'-Dimethoxytrityl)-2'-O-(2-cyanoethoxymethyl) uridine (0.630 g, 1.0 mmol) was dried by repetition of azeotropy with pyridine and toluene to obtain a solution in tetrahydrofuran (5 ml). This solution was added with triethylamine (1.0 ml, 7.1 mmol), and the mixture was cooled to −78° C., and carefully added dropwise with a 0.5 M solution of (4S, 5R)-oxazaphospholidine chloride (6 ml, 3.0 mmol) in tetrahydrofuran at the same temperature, −78° C. The mixture was stirred for 1.5 hours with returning it to room temperature, then diluted with chloroform (400 ml), and added with saturated aqueous sodium hydrogencarbonate (100 ml). The organic layer was separated, and then washed with saturated aqueous sodium hydrogencarbonate (100 ml×2), and the combined washing solution was extracted with chloroform (30 ml×2). The organic layer was dried over anhydrous sodium sulfate, then filtered and concentrated under reduced pressure. The residue was purified by silica gel chromatography [15 g of NH silica gel, toluene/ethyl acetate/triethylamine (60:40:0.1, v/v/v)]. The fractions containing the objective substance were collected, and washed with saturated aqueous sodium hydrogencarbonate (100 ml), and then the organic layer was dried over anhydrous sodium sulfate, filtered and concentrating under reduced pressure to obtain the objective substance (0.520 g, 62%, colorless amorphous).

$^1$H NMR (300 MHz, CDCl$_3$) δ 8.07 (H, d, $^3$J=8.1, 6-H) 7.24-7.28 (14H, m, 5"-Ph, m to OMe of DMTr, Ph of DMTr), 6.76-6.82 (4H, m, o to OMe of DMTr), 5.95 (H, d, $^3$J=1.2 Hz, 1'-H), 5.75 (H, d, $^3$J=6.6 Hz, 5"-H), 5.16 (H, d, $^3$J=8.1 Hz, 5-H), 4.96, 5.01 (2H, 2d, $^3$J=7.2 Hz, —OCH$_2$ of CEM), 4.89 (H, ddd, $^3$J=6.9, 6.9, 8.4 Hz, 3'-H), 4.35 (H, dd, $^3$J=1.2, 4.8 Hz, 2'-H), 4.21 (H, d, $^3$J=8.1 Hz, 4'-H), 3.87-3.94 (3H, m, 4"-H, —OCH$_2$O of CEM), 3.74, 3.77 (6H, 2s, —OMe of DMTr), 3.52-3.60 (3H, m, 5'-H, 6"-H), 3.07-3.13 (H, m, 6"-H), 2.67 (2H, ddd, $^3$J=2.7, 6.5, 6.5 Hz, —CH$_2$CN of CEM), 1.56-1.62 (2H, m, 7"-H), 0.94-1.28 (2H, m, 8"-H)

$^{31}$P NMR (121 MHz, CDCl$_3$) δ 158.2

(b) N$^6$-Acetyl-5'-O-(4,4'-dimethoxytrityl)-3'-O-[(2R,4S,5R)-5-phenyl-tetrahydro-1H,3H-pyrrolo[1,2-c]-1,3,2-oxazaphospholidin-2-yl]-2'-O-(2-cyanoethoxymethyl)adenosine [(Rp)]

N$^6$-Acetyl-5'-O-(4,4'-dimethoxytrityl)-2'-O-(2-cyanoethoxymethyl)adenosine (0.695 g, 1.0 mmol) was added with triethylamine (1.0 ml, 7.1 mmol) and a 0.5 M solution of (4S,5R)-oxazaphospholidine chloride (6 ml, 3.0 mmol) in tetrahydrofuran, and the mixture was stirred at room temperature for 2 hours. The residue was purified by silica gel chromatography [25 g of NH silica gel, toluene/ethyl acetate/triethylamine (20:10:0.03, v/v/v) to obtain the objective substance (0.443 g, 49%, colorless amorphous).

$^1$H NMR (300 MHz, CDCl$_3$) δ 8.77 (H, br.s, 6-NH), 8.61 (H, s, 2-H), 8.26 (H, s, 8-H), 7.20-7.45 (14H, m, 5"-Ph, m to OMe of DMTr, Ph of DMTr), 6.80 (4H, d, $^3$J=9.0 Hz, o to OMe of DMTr), 6.24 (H, d, $^3$J=4.8 Hz, 1'-H), 5.77 (H, d, $^3$J=6.3 Hz, 5"-H), 4.95-5.06 (2H, m, 2'-H, 3'-H), 4.73, 4.83 (2H, 2d, $^3$J=7.2 Hz, —OCH$_2$ of CEM), 4.40 (H, dd, $^3$J=3.0, 6.0 Hz, 4'-H), 3.83-3.92 (H, m, 4"-H), 3.78 (6H, s, —OMe of DMTr), 3.38-3.65 (3H, m, 6'-H, —OCH$_2$O of CEM), 3.41 (H, dd, $^3$J=3.3, 10.5 Hz, 5'-H), 3.06-3.18 (H, m, 6"-H), 2.60 (3H, s, Ac), 2.36 (2H, m, —CH$_2$CN of CEM), 1.59-1.69 (2H, m, 7"-H), 0.88-1.28 (2H, .m, 8"-H)

$^{31}$P NMR (121 MHz, CDCl$_3$) δ 57.0

(c) N$^4$-Acetyl-5'-O-(4,4'-dimethoxytrityl)-3'-O-[(2R,4S,5R)-5-phenyl-tetrahydro-1H,3H-pyrrolo[1,2-c]-1,3,2-oxazaphospholidin-2-yl]-2'-O-(2-cyanoethoxymethyl)cytidine [(Rp)]

N$^4$-Acetyl-5'-O-(4,4'-dimethoxytrityl)-2'-O-(2-cyanoethoxymethyl)cytidine (1.010 g, 1.5 mmol) was added with triethylamine (1.5 ml, 10.5 mmol) and a 0.5 M solution of (4S,5R)-oxazaphospholidine chloride (9.0 ml, 4.5 mmol) in tetrahydrofuran, and the mixture was stirred at room temperature for 1.5 hours. The residue was purified by silica gel chromatography [0.30 g of crude product, 3.0 g of NH silica gel, hexane/ethyl acetate/triethylamine (20:10:0.03, v/v/v→10:30:0.04, v/v/v/v); 0.30 g of crude product, 3.0 g of NH silica gel, hexane/ethyl acetate/triethylamine (20:10:0.03, v/v/v→10:20:0.03, v/v/v); and 1.23 g of crude product, 12.3 g of NH silica gel, hexane/ethyl acetate/triethylamine (20:10:0.03, v/v/v→10:20:0.03, v/v/v)] to obtain the objective substance (0.693 g, 53%, yellow amorphous).

$^1$H NMR (300 MHz, CDCl$_3$) δ 9.68 (H, br.s, 4-NH), 8.54 (H, d, $^3$J=7.5 Hz, 6-H), 7.22-7.42 (14H, m, 5"-Ph, m to OMe of DMTr, Ph of DMTr), 6.88 (H, d, $^3$J=7.5 Hz, 5-H), 6.77-6.84 (4H, m, o to OMe of DMTr), 5.94 (H, s, 1'-H), 5.72 (H, d, $^3$J=6.3 Hz, 5"-H), 4.98, 5.15 (2H, 2d, $^3$J=6.9 Hz, —OCH$_2$ of CEM), 4.84 (H, ddd, $^3$J=4.8, 9.3, 9.3 Hz, 3'-H), 4.26-4.33 (2H, m, 2'-H, 4'-H), 3.86-3.96 (3H, m, 4"-H, —OCH$_2$O of CEM), 3.75, 3.78 (6H, 2s, —OMe of DMTr), 3.50-3.69 (3H, m, 5'-H, 6"-H), 3.04-3.15 (H, m, 6"-H), 2.59-2.78 (2H, m, —CH$_2$CN of CEM), 2.24 (3H, s, Ac), 1.51-1.67 (2H, m, 7"-H), 0.86-1.28 (2H, m, 8"-H)

$^{31}$P NMR (121 MHz, CDCl$_3$) δ 158.0

(d) O$^6$-Cyanoethyl-N$^2$-phenoxyacetyl-5'-O-(4,4'-dimethoxytrityl-3'-O-[(2S,4R,5S)-5-phenyl-tetrahydro-1H,3H-pyrrolo[1,2-c]-1,3,2-oxazaphospholidin-2-yl]-2'-O-(2-cyanoethoxymethyl)guanosine [(Rp)]

O$^6$-Cyanoethyl-N$^2$-phenoxyacetyl-5'-O-(4,4'-dimethoxytrityl)-2'-O-(2-cyanoethoxymethyl)guanosine (0.856 g, 1.0 mmol) was added with triethylamine (1.0 ml, 7.1 mmol) and a 0.5 M solution of (4S,5R)-oxazaphospholidine chloride (6.0 ml, 3.0 mmol) in tetrahydrofuran, and the mixture was stirred at room temperature for 2 hours. The residue was purified by silica gel chromatography [20 g of NH silica gel, toluene/ethyl acetate/triethylamine (80:20:0.1, v/v/v)] to obtain the objective substance (0.447 g, 42%, colorless amorphous).

$^1$H NMR (300 MHz, CDCl$_3$) δ 8.79 (H, br.s, 2-NH), 8.10 (H, s, 8-H), 7.00-7.42 (19H, m, 5"-Ph, m to OMe of DMTr, Ph of DMTr, Ph of Pac), 6.76 (2H, d, $^3$J=6.6 Hz, o to OMe of DMTr), 6.23 (H, d, $^3$J=5.1 Hz, 1'-H), 5.74 (H, d, $^3$J=6.3 Hz, 5"-H), 4.82-5.01 (6H, m, 2'-H, 3'-H, —OCH$_2$ of CEM, —OCH$_2$ of Ce), 4.63 (2H, s, —CH$_2$ of Pac), 4.35 (H, d, $^3$J=2.7 Hz, 4'-H), 3.44-3.90 (12H, m, 5'-H, 4"-H, 6"-H, —OCH$_2$O of CEM, OMe of DMTr), 3.04-3.19 (3H, m, 6"-H, —CH$_2$CN of Ce), 2.48 (2H, t, $^3$J=6.3 Hz, —CH$_2$CN of CEM), 1.59-1.66 (2H, m, 7"-H), 0.88-1.29 (2H, m, 8"-H)

$^{31}$P NMR (121 MHz, CDCl$_3$) δ 156.8

Example 3

The following compounds were synthesized in the same manner as that of Example 2 by using 4R,5S-oxazaphospholidine chloride.

(a) 5'-O-(4,4'-Dimethoxytrityl)-3'-O-[(2S,4R,5S)-5-phenyl-tetrahydro-1H,3H-pyrrolo[1,2-c]-1,3,2-oxazaphospholidin-2-yl]-2'-O-(2-cyanoethoxymethyl)uridine [(Sp)]

5'-O-(4,4'-Dimethoxytrityl)-2'-O-(2-cyanoethoxymethyl)uridine (0.944 g, 1.5 mmol) was added with triethylamine (1.5 ml, 10.5 mmol) and a 0.5 M solution of 4R,5S-oxazaphospholidine chloride (9.3 ml, 4.7 mmol) in tetrahydrofuran, and the mixture was stirred at room temperature for 1.5 hours. The residue was purified by silica gel chromatography [0.30 g of crude product, 3 g of NH silica gel, hexane/ethyl acetate/triethylamine (20:10:0.03, v/v/v→10:10:0.02, v/v/v); and 1.40 g of crude product, 5.5×27 cm, 3.0 g of NH silica gel, hexane/ethyl acetate/triethylamine (20:10:0.03, v/v/v→10:20:0.03, v/v/v)] to obtain the objective substance (0.900 g, 71%, colorless amorphous).

$^1$H NMR (300 MHz, CDCl$_3$) δ 9.24 (H, br.s, 3-NH), 8.11 (H, d, 6-H), 7.24-7.41 (14H, m, 5"-Ph, m to OMe of DMTr, Ph of DMTr), 6.85 (4H, dd, $^3$J=2.1, 9.0 Hz, o to OMe of DMTr), 5.98 (H, d, $^3$J=1.5 Hz, 1'-H), 5.79 (H, d, $^3$J=6.3 Hz, 5"-H), 5.20 (2H, d, $^3$J=8.4 Hz, 5-H), δ 4.81-4.89 (3H, m, 3'-H, —OCH$_2$ of CEM), 4.25-4.32 (2H, m, 2'-H, 4'H), 3.68-3.87 (9H, m, 4"-H, —OCH$_2$ of CEM, —OMe of DMTr), 3.41-3.54 (3H, m, 5'-H, 6"-H), 3.03-3.14 (H, m, 6"-H), 2.46-2.51 (2H, ddd, $^3$J=1.8, 6.0, 6.0 Hz, —CH$_2$CN of CEM), 1.59-1.68 (2H, m, 7"-H), 0.88-1.28 (2H, m, 8"-H)

$^{31}$P NMR (121 MHz, CDCl$_3$) δ 159.4

(b) N$^6$-Acetyl-5'-O-(4,4'-dimethoxytrityl)-3'-O-[(2S, 4R,5S)-5-phenyl-tetrahydro-1H,3H-pyrrolo[1,2-c]-1,3,2-oxazaphospholidin-2-yl]-2'-O-(2-cyanoethoxymethyl)adenosine [(Sp)]

N$^6$-Acetyl-5'-O-(4,4'-dimethoxytrityl)-2'-O-(2-cyanoethoxymethyl)adenosine (0.698 g, 10 mmol) was added with triethylamine (1.0 ml, 7.1 mmol) and a 0.5 M solution of (4R,5S)-oxazaphospholidine chloride (6.0 ml, 3.0 mmol) in tetrahydrofuran, and the mixture was stirred at room temperature for 2 hours. The residue was purified by silica gel chromatography [13 g of NH silica gel, toluene/ethyl acetate/triethylamine (50:50:0.1, v/v/v)] to obtain the objective substance (0.462 g, 51%, colorless amorphous).

$^1$H NMR (300 MHz, CDCl$_3$) δ 8.77 (H, br.s, 6-NH), 8.61 (H, s, 2-H), 8.21 (H, s, 8-H), 7.16-7.42 (14H, m, 5"-Ph, m to OMe of DMTr, Ph of DMTr), 6.76 (4H, d, $^3$J=6.9 Hz, o to OMe of DMTr), 6.22 (H, d, $^3$J=5.1 Hz, 1'-H), 5.79 (H, d, $^3$J=6.6 Hz, 5"-H), 5.07 (H, dd, $^3$J=5.1, 5.1 Hz, 2'-H), 4.98 (H, ddd, $^3$J=4.5, 4.5, 9.6 Hz, 3'-H), 4.85, 4.89 (2H, 2d, $^3$J=7.2 Hz, —OCH$_2$ of CEM), 4.36 (H, dd, $^3$J=3.9, 8.1 Hz, 4'-H), 3.49-3.94 (9H, m, 4"-H, 6"-H, —OCH$_2$O of CEM, —OMe of DMTr), 3.03-3.15 (H, m, 6"-H), 2.61 (3H, s, Ac), 2.48 (2H, t, $^3$J=6.3 Hz, —CH$_2$CN of CEM), 1.56-1.66 (2H, m, 7"-H), 0.89-1.28 (2H, m, 8"-H)

$^{31}$P NMR (121 MHz, CDCl$_3$) δ 156.1

(c) N$^6$-Acetyl-5'-O-(4,4'-dimethoxytrityl)-3'-O-[(2R, 4S,5R)-5-phenyl-tetrahydro-1H,3H-pyrrolo[1,2-c]-1,3,2-oxazaphospholidin-2-yl]-2'-O-(2-cyanoethoxymethyl)cytidine [(Sp)]

N$^4$-Acetyl-5'-O-(4,4'-dimethoxytrityl)-2'-O-(2-cyanoethoxymethyl)cytidine (0.671 g, 1.0 mmol) was added with triethylamine (1.0 ml, 7.1 mmol) and a 0.5 M solution of (4R,5S)-oxazaphospholidine chloride (6.0 ml, 3.0 mmol) in tetrahydrofuran, and the mixture was stirred at room temperature for 1.5 hours. The residue was purified by silica gel chromatography [14 g of NH silica gel, toluene/ethyl acetate/triethylamine (10:20:0.03, v/v/v)] to obtain the objective substance (0.655 g, 75%, yellow amorphous).

$^1$H NMR (300 MHz, CDCl$_3$) δ 9.58 (H, br.s, 4-NH), 8.61 (H, d, $^3$J=7.2 Hz, 6-H), 7.22-7.44 (14H, m, 5"-Ph, m to OMe of DMTr, Ph of DMTr), 6.99 (H, d, $^3$J=7.8 Hz, 5-H), 6.86 (4H, dd, $^3$J=1.8, 8.7 Hz, o to OMe of DMTr), 5.98 (H, s, 1'-H), 5.78 (H, d, $^3$J=6.3 Hz, 5"-H), 4.95, 5.04 (2H, 2d, $^3$J=6.9 Hz, —CH$_2$O of CEM), 4.78 (H, ddd, $^3$J=4.8, 9.3, 9.3 Hz, 3'-H), 4.27-4.34 (H, m, 2'-H, 4'-H), 3.73-3.88 (9H, m, 4"-H, —OCH$_2$O of CEM, —OMe of DMTr), 3.39-3.56 (3H, m, 5'-H, 6"-H), 3.00-3.12 (H, m, 6"-H), 2.49 (2H, t, $^3$J=6.9 Hz, —CH$_2$CN of CEM), 2.24 (3H, s, Ac), 1.58-1.67 (2H, m, 7"-H), 0.86-1.28 (2H, m, 8"-H)

$^{31}$P NMR (121 MHz, CDCl$_3$) δ 159.0

(d) O$^6$-Cyanoethyl-N$^2$-phenoxyacetyl-5'-O-(4,4'-dimethoxytrityl)-3'-O-[(2R,4S,5R)-5-phenyl-tetrahydro-1H,3H-pyrrolo[1,2-c]-1,3,2-oxazaphospholidin-2-yl]-2'-O-(2-cyanoethoxymethyl) guanosine [(Sp)]

O$^6$-Cyanoethyl-N$^2$-phenoxyacetyl-5'-O-(4,4'-dimethoxytrityl)-2'-O-(2-cyanoethoxymethyl)guanosine (1.280 g, 1.5 mmol) was added with triethylamine (1.5 ml, 10.5 mmol) and a 0.5 M solution of 4R,5S-oxazaphospholidine chloride (9.0 ml, 4.5 mmol) in tetrahydrofuran, and the mixture was stirred at room temperature for 1.5 hours. The residue was purified by silica gel chromatography [0.30 g of crude product, 3.0 g of NH silica gel, hexane/ethyl acetate/triethylamine (30:10:0.04, v/v/v→10:20:0.03, v/v/v); and 1.5 g of crude product, 15 g of NH silica gel, hexane/ethyl acetate/triethylamine (30:10:0.04, v/v/v→10:20:0.03, v/v/v)] to obtain the objective substance (0.865 g, 54%, colorless amorphous).

$^1$H NMR (300 MHz, CDCl$_3$) δ 8.77 (H, br.s, 2-NH), 8.13 (H, s, 8-H), 6.98-7.45 (19H, m, 5"-Ph, m to OMe of DMTr, Ph of DMTr, Ph of Pac), 6.76 (2H, d, $^3$J=6.6 Hz, o to OMe of DMTr), 7.80 (H, d, $^3$J=4.8 Hz, 1'-H), 5.76 (H, d, $^3$J=6.6 Hz, 5"-H), 4.75-4.99 (6H, m, 2'-H, 3'-H, —OCH$_2$ of CEM, —OCH$_2$ of Ce), 4.62 (2H, s, —CH$_2$ of Pac), 4.39 (H, d, $^3$J=3.3 Hz, 4'-H), 3.77-3.90 (7H, m, 4"-H, OMe of DMTr), 3.42-3.62 (6H, m, 5'-H, 6"-H, —OCH$_2$O of CEM) 3.03-3.19 (3H, m, 6"-H, —CH$_2$CN of Ce), 2.34 (2H, t, $^3$J=6.3 Hz, —CH$_2$CN of CEM), 1.59-1.75 (2H, m, 7"-H), 0.88-1.28 (2H, m, 8"-H)

$^{31}$P NMR (121 MHz, CDCl$_3$) δ 156.8

In the reactions of Examples 2 and 3, all the ribonucleoside oxazaphospholidines as the objective substances were obtained with high diastereoselectivity.

TABLE 1

| B$^{Pro}$ | | configuration of 8 | isolated yield (%) | dr (Sp:Rp) |
|---|---|---|---|---|
| U | Cl | (2R, 4S, 5R) | 62 | >1:99 |
| A$^{ac}$ | \| | (2R, 4S, 5R) | 49 | >1:99 |
| C$^{ac}$ | P | (2R, 4S, 5R) | 53 | >1:99 |
| G$^{ce}_{pac}$ | O—N | (2R, 4S, 5R) | 42 | >1:99 |
| | Ph  8a | | | |
| U | Cl | (2S, 4R, 5S) | 71 | >99:1 |
| A$^{ac}$ | \| | (2S, 4R, 5S) | 51 | >99:1 |
| C$^{ac}$ | P | (2S, 4R, 5S) | 75 | >99:1 |
| G$^{ce}_{pac}$ | O—N | (2S, 4R, 5S) | 54 | >99:1 |
| | Ph  8b | | | |

Example 4

(a) Phosphorothioate RNA dimers were stereoselectively solid-phase synthesized by using (Rp)- or (Sp)-ribonucleoside oxazaphospholidine as the monomer unit. The reaction process is shown below.

[Formula 8]

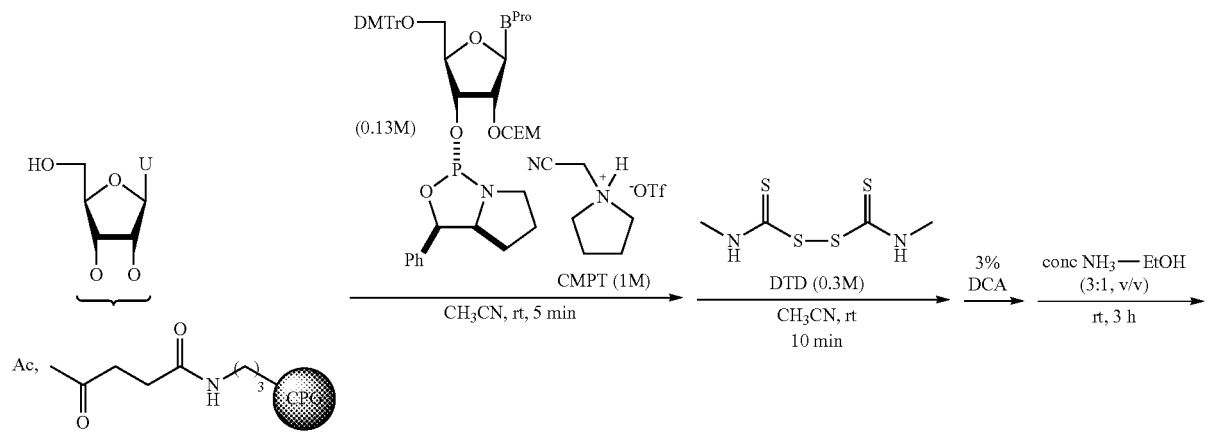

By using CPG as the solid phase carrier, and a succinyl linker as the linker, the 5'-hydroxyl group of uridine on the solid phase carrier and the monomer unit were condensed with a weakly nucleophilic activator, CMPT, then the produced phosphite was sulfurized with DTD and cleaved from the solid phase carrier by a concentrated ammonia/ethanol (3:1, v/v) treatment, and deprotection of the protective groups of the asymmetric auxiliary group and the nucleobase moiety was performed to stereoselectively synthesize a dimmer. The product was analyzed by RP-HPLC in a state that the CEM group was left for ease of quantification of the dimmer to calculated condensing efficiency and diastereoselectivity. As a result, it was confirmed that the condensation reaction advanced at high condensing efficiency sufficiently applicable to synthesis of oligomers, and high diastereoselectivity. Further, in this reaction process, the condensation reaction completed within about 5 minutes, and thus it was confirmed that the reactivity was extremely higher than that observed in the conventional reaction using the TBDMS group, in which 15 minutes was required for the condensation for forming the dimer.

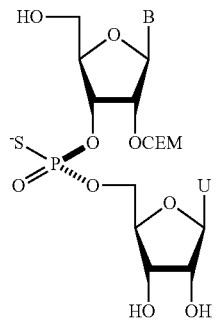

TABLE 2

| entry | monomer ($B^{pro}=$) | product (B=) | coupling yield$^a$ | dr (Sp:Rp)$^a$ |
|---|---|---|---|---|
| 1 | (Rp)-9a (U) | (Sp)-11a (U) | 98% | >1:99 |
| 2 | (Rp)-9b ($A^{ac}$) | (Sp)-11b (A) | 95% | >1:99 |
| 3 | (Rp)-9c ($C^{ac}$) | (Sp)-11c (C) | 96% | >1:99 |
| 4 | (Rp)-9d ($G^{pac^{ce}}$) | (Sp)-11d (G) | 97% | >1:99 |
| 5 | (Sp)-9e (U) | (Rp)-11e (U) | 96% | >99:1 |
| 6 | (Sp)-9f ($A^{ac}$) | (Rp)-11f (A) | 97% | >99:1 |
| 7 | (Sp)-9g ($C^{ac}$) | (Rp)-11g (C) | 95% | >99:1 |
| 8 | (Sp)-9h ($Q^{pac^{ce}}$) | (Rp)-11h (G) | 96% | >99:1 |

$^a$Determined by RP-HPLC.

(b) In the same manner as that of (a) mentioned above, phosphorothioate RNA tetramers (All-(Rp)-[Ups]$_3$U, All-(Sp)-[Ups]$_3$U, All-(Rp)-ApsGpsCpsU, and All-(Sp)-ApsGpsCpsU) were synthesized. The reaction process is shown below.

[Formula 9]

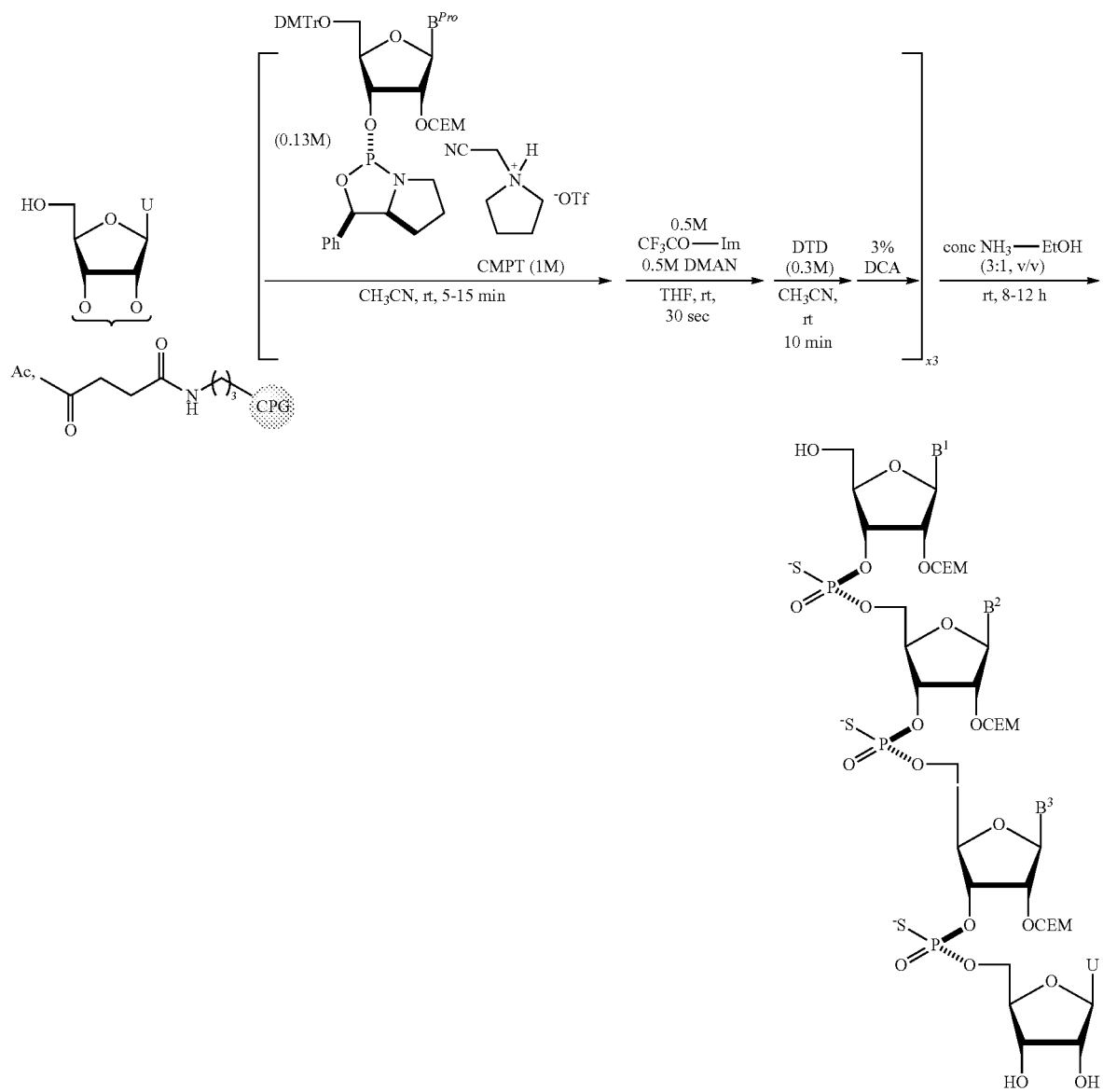

The condensation was performed by using the activator CMPT, and then unreacted 5'-hydroxyl group and the amino group of asymmetric auxiliary group were capped with trifluoroacetylimidazole ($CF_3CO$-Im). The capping was performed in order to suppress synthesis of sequences other than the objective sequence, and reduce the basicity by acylating the amino group of the asymmetric auxiliary group to maintain the acidity in the reaction system. Then, the phosphite was sulfurized with DTD, the DMTr group at the 5'-end was removed (3% DCA), and the monomer unit was further coupled. By repeating the chain extension cycle consisting a series of these reactions, phosphorothioate tetramers having the objective base sequences were synthesized. Finally, the products were cleaved from the solid phase carrier under a basic condition with concentrated ammonia/ethanol (3:1, v/v), and the protective groups were removed. The results are shown in Table 3 below. The average condensing efficiency in the synthesis of All-(Rp)-ApsGpsCpsU performed for comparison according to the conventional method using the TBDMS group as the protective group of the 2'-hydroxyl group and similarly using CMPT was 77%.

TABLE 3

Yield and diastereoselectivity for tetramers

| entry | monomer | product | coupling time | coupling yield[a] | diastereo- selec- tivity[b] |
|---|---|---|---|---|---|
| 1 | U (Sp) | (Rp)-[Ups]$_3$U | 5 min | 91% | >99% |
| 2 | U (Sp) | (Rp)-[Ups]$_3$U | 10 min | 98% | >99% |
| 3 | U (Rp) | (Sp)-[Ups]$_3$U | 10 min | 96% | >99% |
| 4 | A$^{ac}$, C$^{ac}$, G$^{pac^{ce}}$ (Sp) | (Rp)-ApsGpsCpsU | 15 min | 98% | >99% |

TABLE 3-continued

Yield and diastereoselectivity for tetramers

| entry | monomer | product | coupling time | coupling yield[a] | diastereoselectivity[b] |
|---|---|---|---|---|---|
| 5 | $A^{ac}, C^{ac}, G^{pac}_{ce}$ (Rp) | (Sp)-ApsGpsCpsU | 15 min | 94% | >99% |

[a]Average coupling yields were determined by RP-HPLC for entry 1, 3, 5 and by DMTr+ assay for entry 2, 4.
[b]Determined by RP-HPLC.

(c) In the same manner as that mentioned above, All-(Rp)- and -(Sp)-[Ups]$_{11}$U were synthesized as phosphorothioate RNA dodecamers. The reaction process is shown below.

were left. The main peak considered to contain the objective substance was separated and purified, and then the product was desalted by lyophilization with sterilized water repeated three times, and treated with a 0.5 M solution of TBAF containing 0.5% nitromethane for 5 hours to remove the CEM group for deprotection. TBAF was removed by purification with Sep-Pak, and the solvent was evaporated by lyophilization. Then, the product was treated with a 80% acetic acid solution for 1 hour to remove the DMTr group for deprotection. The product was desalted by purification with Sep-Pak, the main peak obtained in RP-HPLC considered to contain the objective substance was separated and purified, and the product was desalted by lyophilization with sterilized water

[Formula 10]

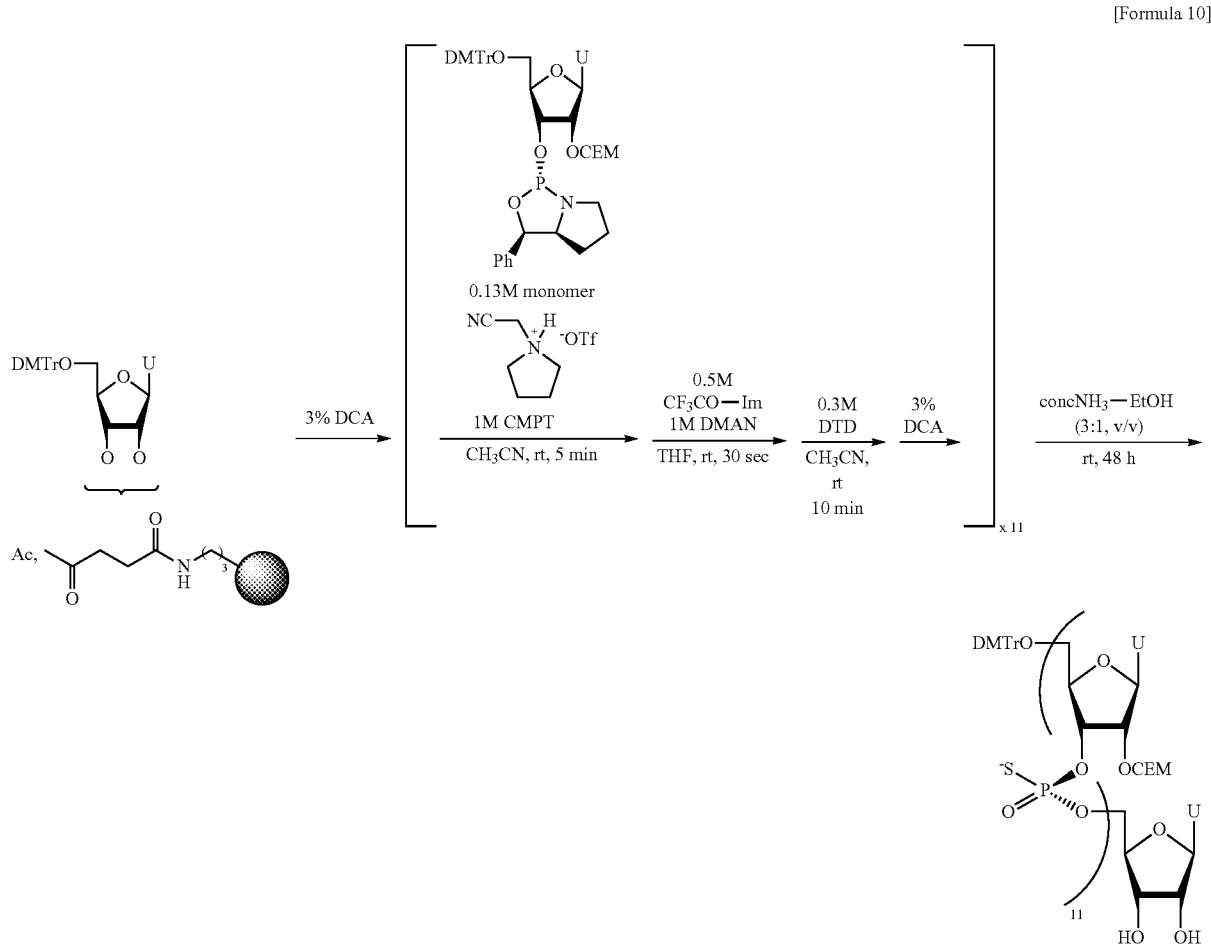

The average condensation yield calculated after the synthesis on the basis of quantification of DMTr was 99% for the both cases of the Rp-dodecamer and the Sp-dodecamer. Favorable average condensing efficiency was also obtained even when the RNA oligomers were synthesized by using CMPT having low nucleophilicity. Each oligomer was cleaved from the solid phase carrier by a treatment with concentrated ammonia/EtOH (3:1, v/v) for 4 hours, and filtered to remove the solid phase carrier, and the product was treated with ammonia again to remove the protective groups. Then, after the solvent of the reaction mixture was evaporated to a volume of about 2 ml, the product was analyzed by RP-HPLC in a state that the CEM group and the DMTr group repeated three times to obtain the objective substance. The product was identified by MALDI-TOF-MAS and confirmed to be the objective substance.

All-(Rp)-(Ups)$_{11}$U 12-mer
 Isolation yield: 12% (yield was calculated by using extinction coefficient $\epsilon_{260}$=120320 (/M/cm))
 MALDI-TOF MAS: m/z calcd for $C_{108}H_{131}N_{24}O_{83}P_{11}S_{11}$— [(M-H).] 3785.09. found 3788.62

All-(Sp)-(Ups)$_{11}$U 12-mer
 Isolation yield: 14% (yield was calculated by using extinction coefficient $\epsilon_{260}$=120320 (/M/cm))
 MALDI-TOF MAS: m/z calcd for $C_{108}H_{131}N_{24}O_{83}P_{11}S_{11}$— [(M-H).] 3785.09. found 3789.25

TABLE 4

| entry | target sequence | coupling conditions activator | monomer | total ave. yield[a] | diastereo- selectivity[b] |
|---|---|---|---|---|---|
| 1 | All-(Rp)-(Ups)$_{11}$U | CMPT | (Sp)-U | 99% | >99% |
| 2 | All-(Sp)-(Ups)$_{11}$U | CMPT | (Rp)-U | 99% | >99% |

[a]Determined by DMTr[+]assay.
[b]Determined by RP-HPLC.

Example 5

All-(Rp)- and -(Sp)-(CpsApsGpsU)$_3$ containing four kinds of nucleobases were synthesized. Average condensing efficiency was calculated on the basis of quantification of DMTr, and it was found that the average condensing efficiency was 90% for the Rp-dodecamer and 93% for the Sp-dodecamer. The main peak obtained in RP-HPLC was separated and purified, then the CEM group was removed with TBAF, and it was confirmed by MALDI-TOF-MAS that the product was the objective substance.
All-(Sp)-[CpsApsGpsU]$_3$
Isolation yield: 1% (calculated by using extinction coefficient $\epsilon_{260}$=124000 (/M/cm))
MALDI-TOF-MASS: m/z calcd for $C_{114}H_{141}N_{45}O_{71}P_{11}S_{11}{}^-$ [(M-H)$^-$] 3968.29. found 3970.75

It was estimated that the reduced isolation yield compared with that obtained in the preparation of All-(Sp)-[Ups]$_{11}$U was due to the low reactivity of the cytidine monomer. Therefore, All-(Rp)-(CpsApsGpsU)$_3$ was similarly synthesized by repeating twice the condensation reaction using the cytidine monomer (double coupling for cytidine monomer, 15 minutes×2). As a result, the condensing efficiency was improved by about 10% for each time, and the average condensation yield of the dodecamer calculated on the basis of quantification of DMTr was improved as high as 92%. The main peak obtained in RP-HPLC was separated and purified, then the CEM group was removed with TBAF, and it was confirmed by MALDI-TOF-MAS that the product was the objective substance.
All-(Rp)-[CpsApsGpsU]$_3$
Isolation yield: 1% (calculated by using extinction coefficient $\epsilon_{260}$=124000 (/M/cm))
MALDI-TOF-MASS: m/z calcd for $C_{114}H_{141}N_{45}O_{71}P_{11}S_{11}{}^-$ [(M-H)$^-$] 3968.29. found 3969.15

Example 6

Study on Activator

Where large scale synthesis of phosphorothioate RNAs using an automatic nucleic acid synthesizer is contemplated aiming at application thereof as RNAi medicaments, the double coupling cannot be considered to be a practical method. A condensing efficiency obtained was also insufficient for synthesis of RNA oligomers, and moreover, the reactivity of the cytidine monomer should be improved. For purpose of improvement of the condensation reaction efficiency of the cytidine monomer unit, the activator used for the condensation reaction was studied. The activator was investigated by synthesizing a model sequence, All-(Rp)-CpsCpsCpsU tetramer, by using an acid-azole complex, N-phenylimidazolium triflate (PhIMT), as the activator which successfully realized high condensation reaction efficiency in the precedent researches in which the TBDMS group was introduced into the 2'-hydroxyl group.

[Formula 11]

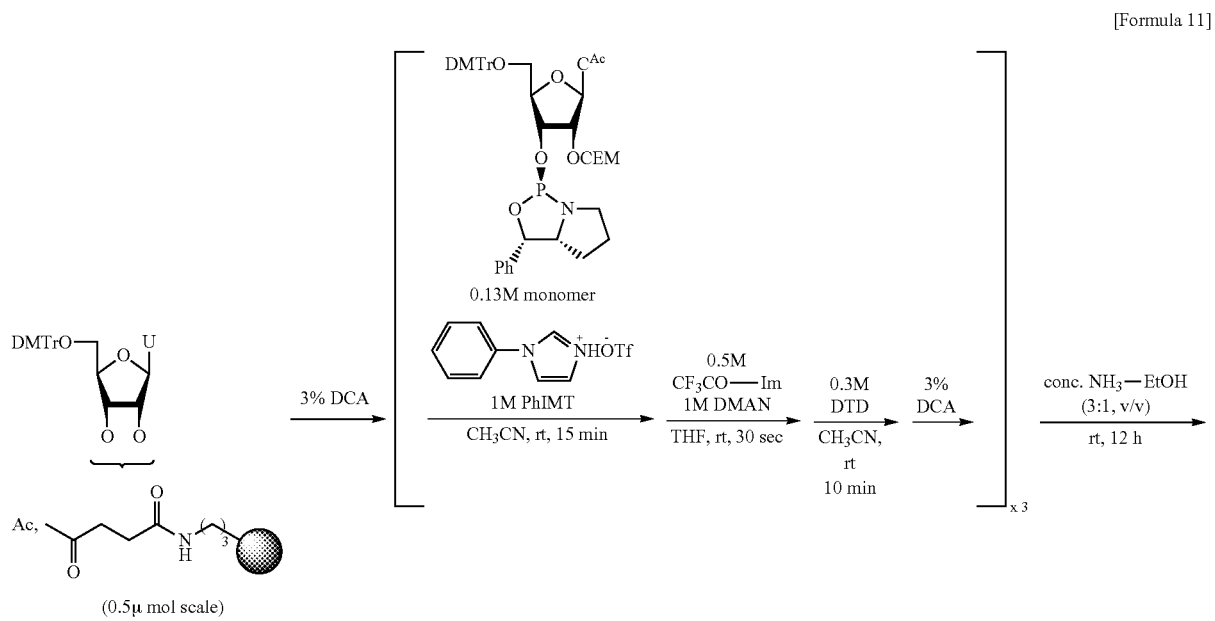

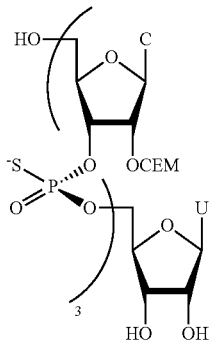

TABLE 5

| entry | monomer | activator | solid support | coupling yield[a] 2 mer | 3 mer | 4 mer |
|---|---|---|---|---|---|---|
| 1 | $C^{zc}$ (Sp) | CMPT | CPG | 88% | 78% | 76% |
| 2 | $C^c$ (Sp) | PhIMT | CPG | 93% | 89% | 86% |

[a]Determined by DMTr+ assay.

The tetramer was synthesized by using highly nucleophilic PhIMT as the activator. The HPLC profile is shown in FIG. 1.

Figure 2:
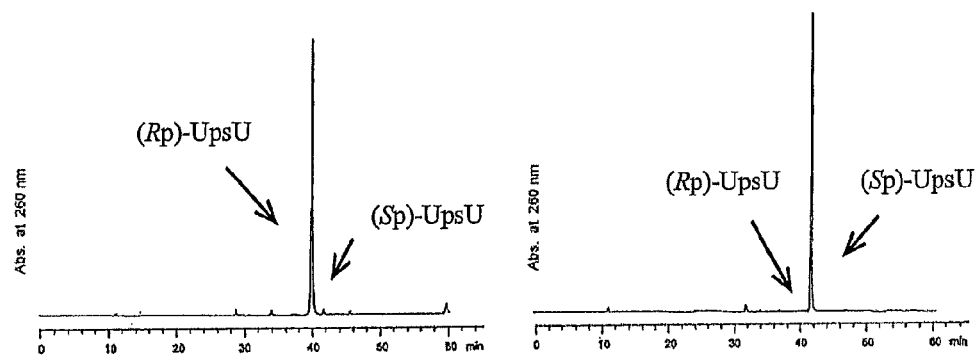
FIG. 2 shows the HPLC profiles of the phosphorothioate RNA dimers obtained in Example 6.

The average condensing efficiency for the tetramer calculated from quantification of DMTr after the synthesis was 89%, and thus markedly improved compared with that obtained with CMPT having low nucleophilicity, and favorable reactivity sufficiently applicable to synthesis of oligomers could be obtained (entry 2). However, since PhIMT is a highly nucleophilic activator, epimerization may advance. Therefore, UpsU dimers were then synthesized by using PhIMT as the activator, and stereoselectivity for each diastereomer was estimated. The HPLC profiles of the dimers are shown in FIG. 2.

[Formula 12]

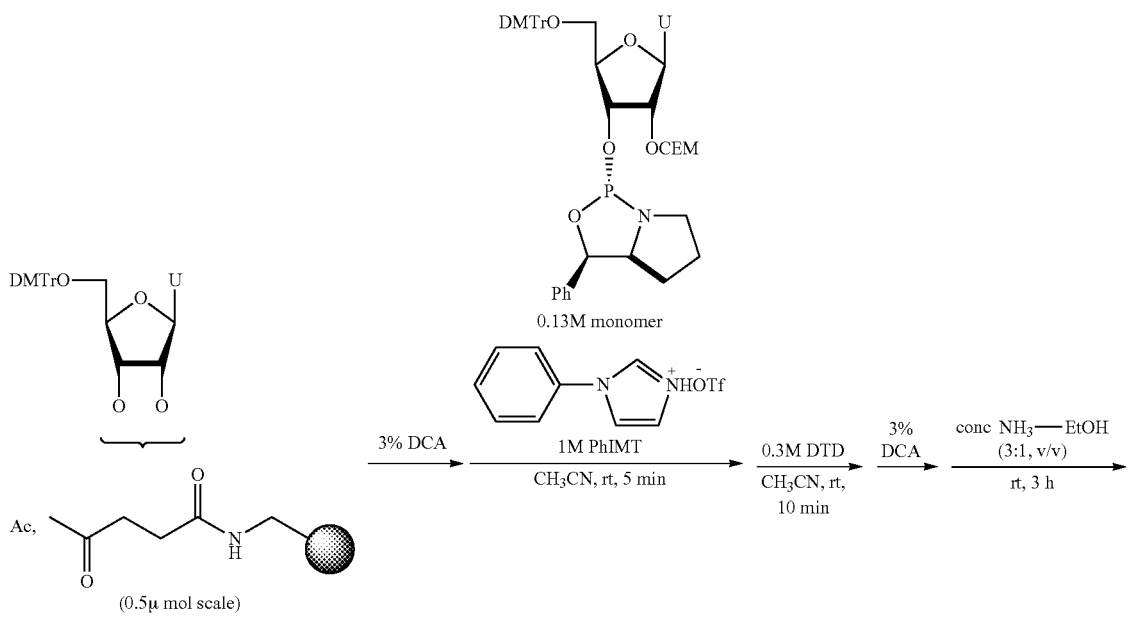

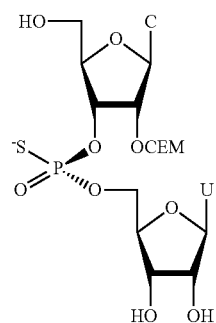

TABLE 6

| entry | target sequence | coupling conditions | | ave. yield[a] | diastereo-selectivity[a] |
|---|---|---|---|---|---|
| | | activator | monomor | | |
| 1 | (Rp)-UpsU | PhIMT | (Sp)-U | 98% | 98% |
| 2 | (Sp)-UpsU | PhIMT | (Rp)-U | 97% | >99% |

[a]Determined by RP-HPLC.

(Rp)- and (Sp)-UpsU dimers were synthesized by using PhIMT as an activator, and stereoselectivity of the condensation reaction was calculated. The stereoselectivity was estimated by identifying the diastereomer on the basis of retention time observed in the RP-HPLC analysis. As a result, the stereoselectivity values calculated from the area values of the HPLC profiles were 98.0% for the Rp-dimer and 99.7% for the Sp-dimer (entries 1 and 2). It was found that favorable stereoselectivity was also given under this synthesis condition utilizing the CEM group as the protective group.

The above study on the condition revealed that, by using PhIMT as the activator, the condensation reaction efficiency was successfully improved, and favorable stereoselectivity was given. It was considered that this result suggested that the use of PhIMT was satisfactorily applicable to the synthesis of RNA oligomers. Accordingly, it was decided to synthesize RNA oligomers containing four kinds of nucleobases by using PhIMT as the activator.

Example 7

Synthesis of All-(Rp)- and -(Sp)-(CpsApsGpsU)$_3$ dodecamers using PhIMT as activator As a result of the study on the activator used in the condensation reaction, when the highly nucleophilic activator, PhIMT, was used, the reactivity of the cytidine monomer unit was markedly improved, and condensing efficiency and stereoselectivity sufficiently applicable to synthesis of RNA oligomers were given. On the basis of the above results, phosphorothioate RNA oligomers containing four kinds of nucleobases were synthesized with change of the activator from CMPT to PhIMT.

[Formula 13]

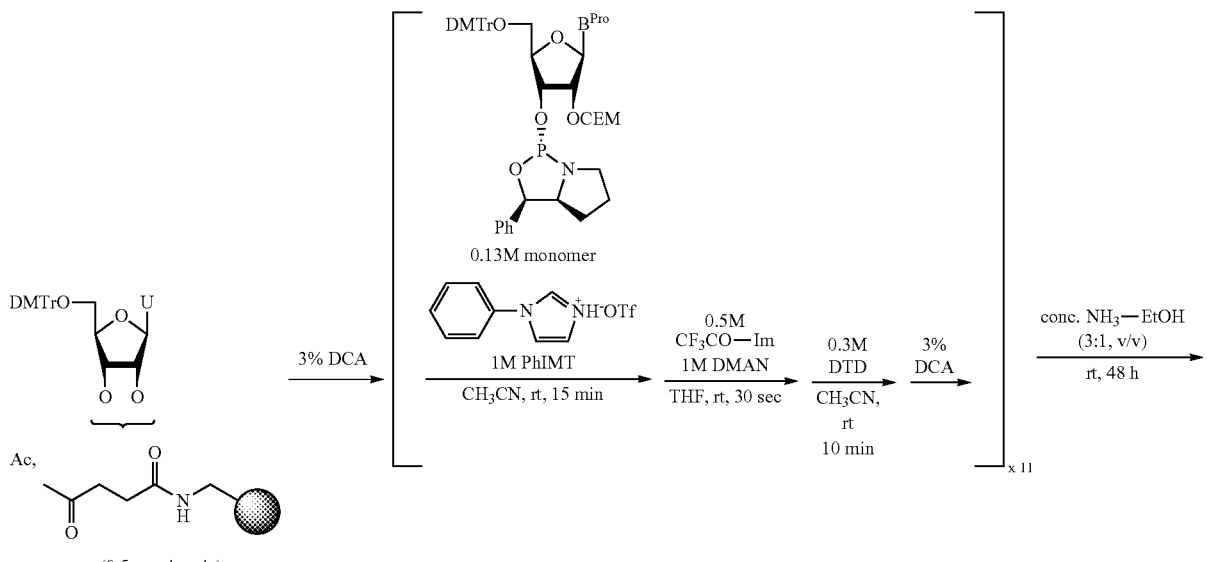

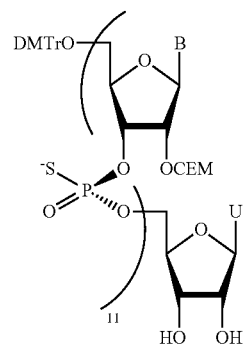

5'-(CAGU)$_3$-3'

B$^{pro}$ = A$^{ac}$, C$^{ac}$, G$^{ce,pac}$, U

TABLE 7

| entry | resin | coupling conditions activator | monomor | ave. yield[a] A | C | G | U | total ave. yield[a] | diastereo-selectivity[b] |
|---|---|---|---|---|---|---|---|---|---|
| 1 | CPG | CMPT | (Rp) | >99% | 80% | 94% | 97% | 93% | >99% |
| 2 | HCP | PhIMT | (Rp) | 98% | 92% | >99% | 97% | 97% | >99% |
| 3 | CPG | CMPT | (Sp) | >99% | 68% | 96% | 97% | 90% | >99% |
| 4 | CPG | CMPT | (Sp) | >99% | 75%[c] | 95% | 96% | 92% | >99% |
| 5 | HCP | PhIMT | (Sp) | 97% | 86% | 95% | 96% | 94% | 98% |

[a]Determined by DMTr[+] assay.
[b]Determined by RP-HPLC.
[c]Cytidine coupling was performed with double coupling.

Figure 3:
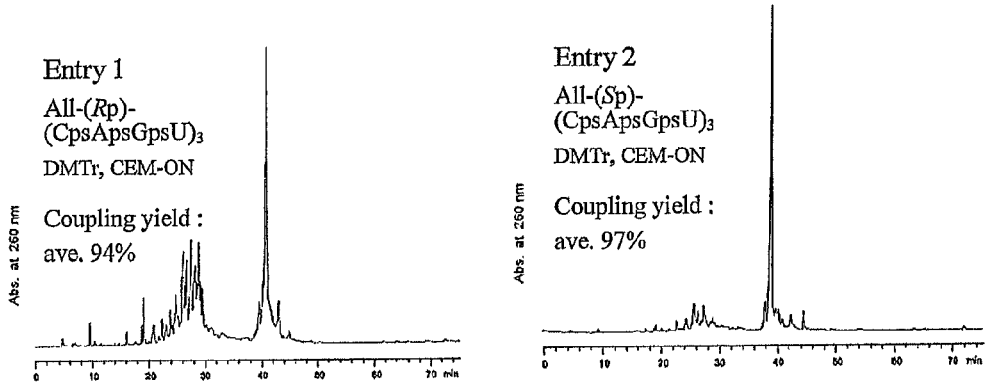
FIG. 3 shows the HPLC profiles of the phosphorothioate RNA dodecamers obtained in Example 7.

Solid phase synthesis of All-(Rp)- and -(Sp)-(CpsApsGpsU)₃ dodecamers was performed by using PhIMT as the activator. The HPLC profiles of the resulting dodecamers are shown in FIG. 3. As a result, the condensation reaction efficiency of the cytidine introduction step was successfully improved by about 10% for both of the Rp-dodecamer and the Sp-dodecamer (Table 7, entries 2 and 5). The peaks obtained in RP-HPLC that were considered to contain the objective substances were separated and purified, and repeatedly subjected to lyophilization with sterilized water three times. As described above, it was demonstrated that when the highly nucleophilic activator, PhIMT, was used, the reactivity of the cytidine monomer was markedly improved, and phosphorothioate RNA oligomers were stereoselectively synthesizable with extremely favorable condensing efficiency.

Example 8

Synthesis and Deprotection of Phosphorothioate RNA Dodecamers

As phosphorothioate RNA dodecamers, All-(Rp)- and -(Sp)-(CpsApsGpsU)₃ dodecamers were synthesized. The average condensation yield calculated after the synthesis on the basis of quantification of DMTr was 94% for the Rp-dodecamer, and 97% for the Sp-dodecamer. Favorable average condensing efficiency was obtained by synthesizing the RNA oligomers using a highly nucleophilic activator, PhIMT. Each oligomer was cleaved from the solid phase carrier by a treatment with concentrated ammonia/EtOH (3:1, v/v) for 4 hours, and then filtered to remove the solid phase carrier, and

TABLE 8

| entry | 2'-substituent | target sequence | coupling conditions activator | monomor | ave. yield[a] C | total ave. yield[a] |
|---|---|---|---|---|---|---|
| 1 | 2'-OTBDMS | (Rp)-r(GAUUCAGCGU) | PhIMT (0.5M) | (Sp)-C[ac] (0.2M) | 71% | 90% |
| 2 | 2'-OCEM | (Rp)-r(CpsApsGpsU)₃ | PhIMT (1.0M) | (Sp)-C[ac] (0.13M) | 86% | 94% |

[a]Determined by DMTr[+] assay.

In the synthesis of phosphorothioate RNA oligomers containing four kinds of nucleobases using the highly nucleophilic PhIMT as the activator, when the sterically small CEM group was used as the protective group of the 2'-hydroxyl group, a condensing efficiency higher by about 10% was successfully obtained compared with the conventional method using the TBDMS group, which is a protective group having significant steric hindrance (entries 1 and 2).

As described above, it was found that the reactivity of the cytidine monomer unit significantly changed depending on stereochemical environment of the 2'-hydroxyl group, as well as on the basicity of the base moiety. Thus, it was demonstrated that, in order to obtain sufficient condensation reaction efficiency in the synthesis of phosphorothioate RNA oligomers, it was extremely important to use the sterically small CEM group as the protective group of the 2'-hydroxyl group together with a highly nucleophilic activator.

the product was treated with ammonia again to remove the protective groups. Then, after the solvent of the reaction mixture was evaporated to a volume of about 2 ml, and the product was analyzed by RP-HPLC in a state that the CEM group and the DMTr group were remained uncleaved. The main peak that was considered to contain the objective substance was separated and purified, and then the product was desalted by lyophilization with sterilized water repeated three times, and treated with a 0.5 M solution of TBAF containing 0.5% nitromethane for 5 hours to remove the CEM group for deprotection. TBAF was removed by purification with Sep-Pak, and the solvent was evaporated by lyophilization. Then, the product was treated with a 80% acetic acid solution for 1 hour to remove the DMTr group for deprotection. The product was desalted by purification with Sep-Pak, the main peak obtained in RP-HPLC that was considered to contain the objective substance was separated and purified, and the product was desalted by lyophilization with sterilized water repeated three times to obtain the objective substance. The product was identified by MALDI-TOF-MAS and confirmed to be the objective substance.

All-(Rp)-(CpsApsGpsU)₃ 12-mer

Isolation yield: 5% (calculated by using extinction coefficient $\varepsilon_{260}=124000$ (/M/cm))

MALDI-TOF MAS: m/z calcd for $C_{108}H_{131}N_{24}O_{83}P_{11}S_{11}$— [M-H).] 3968.29. found 3971.19

All-(Sp)-(CpsApsGpsU)₃ 12-mer

Isolation yield: 10% (calculated by using extinction coefficient $\varepsilon_{260}=124000$ (/M/cm))

MALDI-TOF MAS: m/z calcd for $C_{108}H_{131}N_{24}O_{83}P_{11}S_{11}$— [M-H).] 3968.29. found 3972.53

The solid phase synthesis in the aforementioned reaction was performed by repeating the following steps (i) to (viii).

(i) 3% Dichloroacetic acid (DCA)/dichloromethane, 15 second×4

(ii) Washing (dichloromethane and then acetonitrile) and drying (iii) Condensation (0.13 M monomer and 1 M CMPT and 1 M PhIMT in anhydrous acetonitrile), 5 to 15 minutes (1 or 2 times)

(iv) Washing ($CH_3CN$) and drying (v) Capping (0.5 M $CF_3CO$-Im and 1 M 1,8-bis-(dimethylamino)naphthalene (DMAN) in anhydrous tetrahydrofuran), 30 seconds (vi) Washing (tetrahydrofuran) and drying (vii) Sulfurization (0.3 M dimethyl thiuram disulfide (DTD) in anhydrous acetonitrile), 10 minutes (viii) Washing ($CH_3CN$) and drying Condensation time was 5 minutes for the dimmers, 10 minutes and 15 minutes for [Ups]₃U and ApsGpsCpsU, respectively, among the tetramers, and 15 minutes for the dodecamers. Capping was performed in the synthesis of the tetramers and the dodecamers. After chain length was extended by repeating the steps, the product was subjected to an ammonia treatment in a state that the 5'-O-DMTr group was remained uncleaved or removed. The 5'-O-DMTr group was removed by a treatment with 3% DCA/dichloromethane (15 seconds×4), and the product was washed with dichloromethane. Then, concentrated ammonia/ethanol (3:1, v/v, 6 ml) was added to the product, the reaction vessel was sealed with a stopper, and then ammonia treatment was performed for 3 hours for the dimers, 8 hours or 12 hours for the tetramers, and 48 hours for the dodecamers.

As for the dimers and the tetramers, after ammonia was evaporated, the mixture was lyophilized, and the residue was added with sterilized water, filtered and analyzed by RP-HPLC (Senshu-Pak C18, Condition A for the dimmers, Condition B for the tetramers). As for the dodecamers, the solution was evaporated under reduced pressure to a volume of about 2 ml, and analyzed by RP-HPLC (Senshu-Pak C18 or Waters C18, Condition C or D for the dodecamers). As for the tetramers and the dodecamers, they were isolated and purified by RP-HPLC, the residue was desalted by lyophilization with sterilized water repeated three times, and the tetramers were stirred in a 0.5 M solution of TBAF in DMSO containing 0.5% $CH_3NO_2$ (10 ml) at room temperature for 5 hours, or the dodecamers were stirred in a 0.5 M solution of TBAF in DMSO containing 0.5% $CH_3NO_2$ (400 μl) at room temperature for 5 hours. A 0.1 M TEAA buffer (pH 7, 40 ml) was added to terminate the reaction, and the products were analyzed by RP-HPLC (tetramers: Senshu-Pak C18, Condition B, dodecamers: Senshu-Pak C18 or Waters C18, Condition D).

For the reverse phase HPLC (RP-HPLC), PEGASIL ODS 5 μm column (120 Å, 4.0 mm×150 mm, Senshu Pak) or μBondasphere C18 5 μm column (100 Å, 3.9 mm×150 mm, Waters) was used as the column. As the elution condition, there was used Condition A; 0 to 20% acetonitrile in 0.1 M triethylammonium acetate (TEAA) buffer (pH 7.0), 30° C., 60 minutes, 0.5 mL/minute; Conditions B: 0 to 30% acetonitrile in 0.1 M triethylammonium acetate (TEAA) buffer (pH 7.0), 30° C., 90 minutes, 0.5 mL/minute; Condition C: 0 to 25% acetonitrile in 0.1 M TEAA buffer (pH 7.0), 30° C., 75 minutes, 0.5 mL/minute; Condition D: 0 to 75% acetonitrile in 0.1 M TEAA buffer (pH 7.0), 30° C., 75 minutes, 0.5 mL/minute; or Condition E: 0 to 30% acetonitrile in 0.1 M TEAA buffer (pH 7.0), 30° C., 60 minutes, 0.5 mL/minute.

Each dodecamer was desalted using Sep-Pak (registered trademark) tC18 by elution with 80% aqueous acetonitrile. A solution containing the resulting dodecamer was lyophilized, and stirred at room temperature in a 80% acetic acid solution for 1 hour. A 2 M TEAA buffer (pH 7, 20 ml) was added to terminate the reaction, and desalting was performed in Sep-Pak (registered trademark) tC18 by elution with 40% aqueous acetonitrile. After acetonitrile in the resulting solution was evaporated under reduced pressure, the residue was analyzed by RP-HPLC (Senshu-Pak C18 or WatersC18, Condition D). The dodecamer was isolated and purified by RP-HPLC, and desalted by lyophilization with sterilized water repeated three times to obtain the objective RNA oligomer. The resulting RNA oligomer was identified to be the objective substance by MALDI-TOF-MASS.

Example 9

Deprotection condition for the CEM group was studied.

[Formula 14]

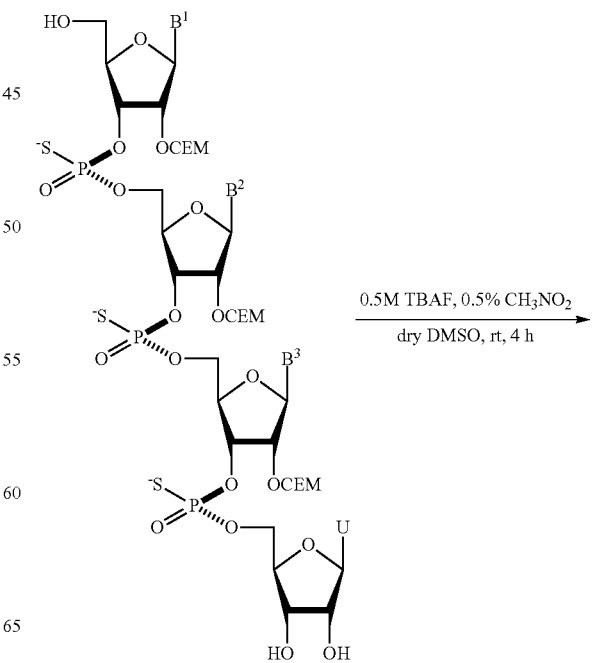

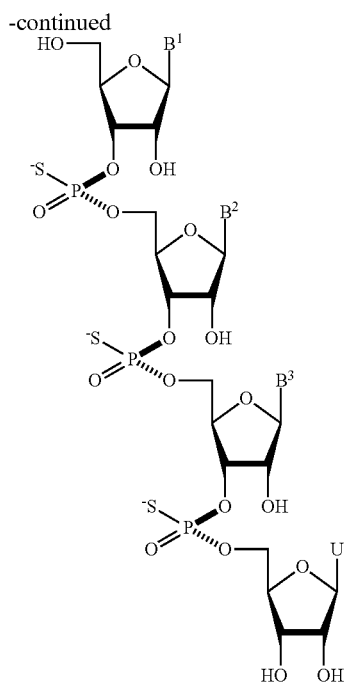

Although the CEM group is selectively removed with TBAF, several percents of desulfurization of phosphorothioate may be observed at the time of the deprotection reaction with TBAF. It is considered that this is because residue of the asymmetric auxiliary group acts as a catalyst to promote the desulfurization reaction. Since the desulfurization can be remarkably suppressed by performing separation and purification by RP-HPLC, the tetramer was isolated and purified, and then was subjected to the deprotection reaction. Deprotection of the CEM group was performed by a treatment with 0.5M TBAF according to the method described in the literature (Nucleic Acids Res., 35, pp. 3287-3296, 2007). In the deprotection reaction, 0.5% nitromethane was added to suppress the addition of acrylonitrile to the nucleobase moiety, which acrylonitrile was a by-product of the reaction for removing CEM. When the product was analyzed by RP-HPLC after the deprotection reaction, it was found that the deprotection reaction quantitatively advanced, and any side reaction such as modification of the nucleobase moiety and desulfurization was not observed.

Example 10

Enzyme Resistance of Phosphorothioate RNA

Enzymatic degradation with nP1 was performed as follows. An aqueous solution (20 µl, pH 7.2) containing the isolated and purified (CpsApsGpsU)$_3$ 12-mer (1.0 nmol), nP1 (1 unit), 50 mM CH$_3$COONa, and 1 mM ZnCl$_2$ was left at a constant temperature of 37° C. for 16 hours. The reaction mixture was added with 0.1 M TEAA buffer (pH 7, 80 µl), and then left at a constant temperature of 100° C. for 1 minute to inactivate the enzyme. The residue was collected by filtration and analyzed by RP-HPLC (Senshu-Pak C18 or Waters C18, Condition E).

Enzymatic degradation with SVPDE was performed as follows. An aqueous solution (20 µl, pH 8.5) containing the isolated and purified (CpsApsGpsU)$_3$ 12-mer (1.0 nmol), SVPDE (0.1×10$^{-3}$ unit), 100 mM Tris-HCl, and 15 mM MgCl$_2$ was left at a constant temperature of 37° C. for 16 hours. The reaction mixture was added with 0.1 M TEAA buffer (pH 7, 80 µl) and then left at a constant temperature of 100° C. for 1 minute to inactivate the enzyme. The residue was collected by filtration and analyzed by RP-HPLC (Senshu-Pak C18 or Waters C18, Condition E).

As the snake venom phosphodiesterase, that purchased from Sigma was used, and as the nuclease P1, that purchased from Yamasa was used.

By confirming enzyme resistance of each synthesized phosphorothioate RNA dodecamer, the absolute configuration of the phosphorus atom was determined. Two kinds of enzymes, a 3'-exo-nucleases, SVPDE, and an endonuclease, nP1, were used for determination of stereochemistry. SVPDE and nP1 are known as enzymes that selectively hydrolyze phosphorothioate diester bonds of Rp-oligomers and Sp-oligomers, respectively. As mentioned in the aforementioned experimental method, each oligomer was subjected to the enzymatic reaction by being left at a constant temperature of 37° C. for 16 hours. Then, after the enzyme was inactivated, analysis was performed by RP-HPLC.

Figure 4:
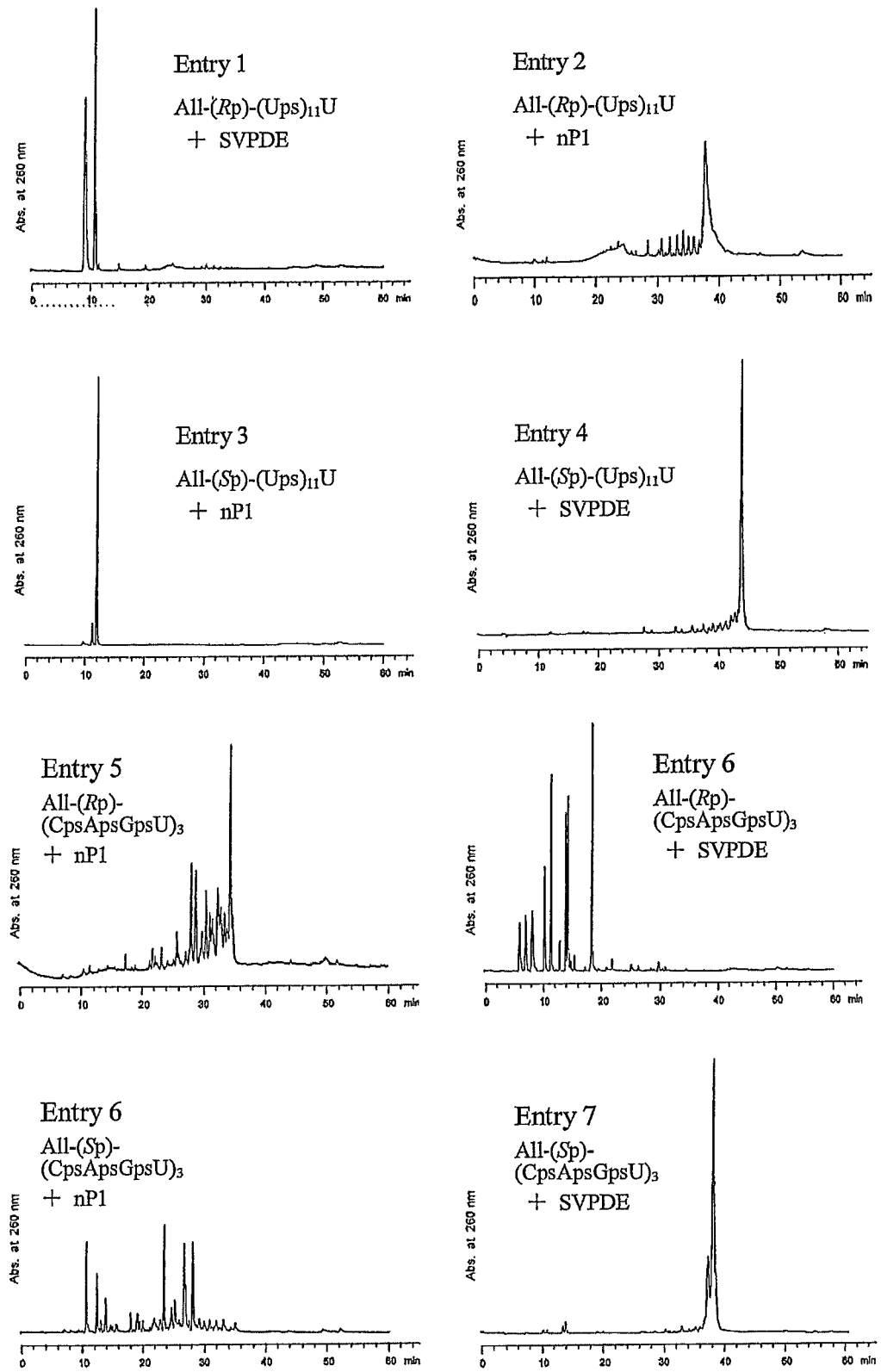
FIG. 4 shows the results of investigation of enzyme resistance of the phosphorothioate RNA dodecamers.

As a result, the All-(Rp)-(Ups)$_{11}$U dodecamer and All-(Rp)-(CpsApsGpsU)$_3$ dodecamer as the oligomer were completely degraded enzymatically with SVPDE, and the All-(Sp)-(Ups)$_{11}$U dodecamer and the All-(Sp)-(CpsApsGpsU)$_3$ dodecamer as the oligomer were completely degraded enzymatically with nP1. The results are shown in FIG. 4. From these results, it was revealed that the absolute configuration of each synthesized RNA oligomer was Rp- or Sp-configuration.

Example 11

Analysis of Melting Temperature (Tm) of Duplex Sequence of Phosphorothioate RNA Containing Four Kinds of Nucleobases Method for Measuring Melting Temperature of r(CAGU)$_3$-r(ACUG)$_3$ Duplex Sequence The isolated and purified All-(Rp)-(CpsApsGpsU)$_3$ or All-(Sp)-(CpsApsGpsU)$_3$, or stereo-random (CpsApsGpsU)$_3$ or (CpoApoGpoU)$_3$, and (ApoCpoUpoG)$_3$ in an amount of 0.45 nmol each were dissolved in an aqueous solution (200 µl, pH 7) containing 10 mM phosphoric acid, 100 mM NaCl, and 0.1 mM EDTA. The oligomer solution was degassed under reduced pressure for 10 minutes, added to octuplet cells in a volume of 165 µl, heated from room temperature to 90° C. at a rate of 5° C./minute, maintained at 90° C. for 10 minutes, and cooled to 0° C. at a rate of −2° C./minute to attain annealing. The oligomer solution was left standing at 0° C. for 90 minutes, and then absorbance thereof was measured at 260 nm at 0.5° C. intervals under a nitrogen flow, with raising the temperature to 90° C. at a rate of 0.5° C./minute.

Figure 5:
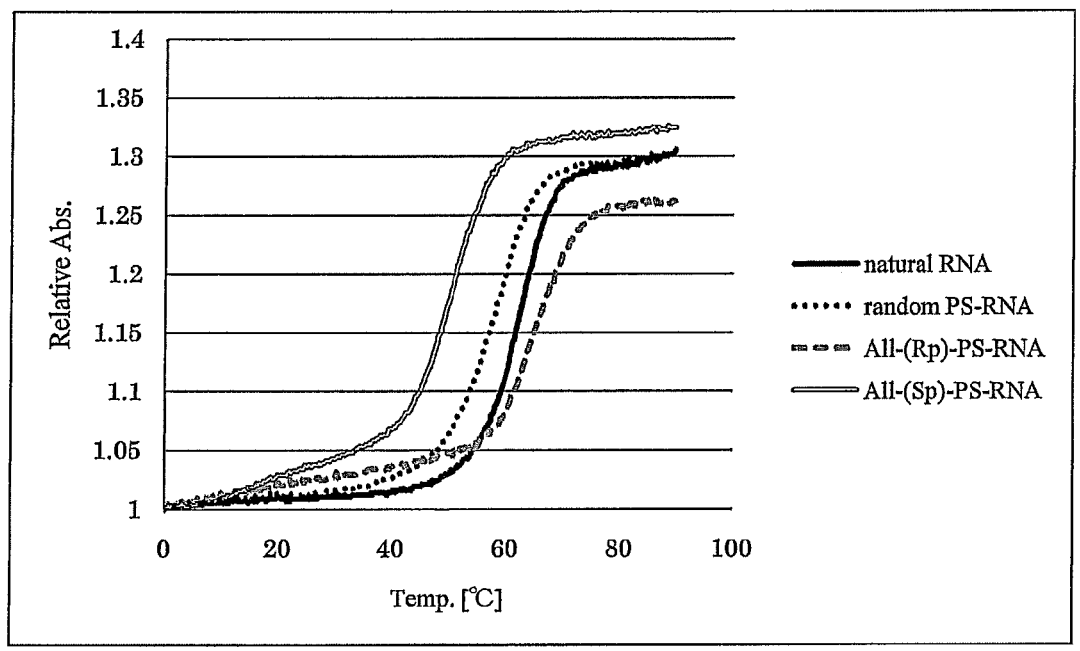
FIG. 5 shows the melting profiles of All-(Rp)- and -(Sp)-(CpsApsGpsU)$_3$-r(ApoCpoUpoG)$_3$.

Melting temperatures (Tm) of duplex sequences formed by the All-(Rp)- or -(Sp)-(CpsApsGpsU)$_3$ dodecamer synthesized by the preparation method of the present invention and a naturally-occurring RNA dodecamer having a complementary sequence were measured. In order to study the influence of the absolute configuration on the phosphorus atom on the duplex sequence-forming ability in detail, duplex sequence-forming abilities of the naturally occurring type RNA dodecamer and now stereocontrolled (CpsApsGpsU)₃ RNA dodecamer, of which stereochemistry on the phosphorus atom was not controlled, were also evaluated. Melting temperature of duplex sequence was measured in a 10 mM phosphate buffer, 100 mM NaCl, closer to the physiological condition. The results are shown in FIG. 5 and Table 9.

TABLE 9

| No. | Duplex sequence | Calculation method | Tm | ΔTm |
|---|---|---|---|---|
| 1 | ntRNA-ntRNA | Median method | 61.65 | 0 |
| 2 | random ps-RNA-ntRNA | Median method | 57.48 | −4.17 |
| 3 | All-(Rp)ps-RNA-ntRNA | Median method | 65.38 | 3.73 |
| 4 | All-(Sp)ps-RNA-ntRNA | Median method | 50.94 | −10.71 |

Tm value of the duplex sequence formed with All-(Rp)-(CpsApsGpsU)₃ dodecamer was 65.38° C., and was higher than that of the duplex sequence formed with the naturally occurring type RNA by 3.7° C., and it was found that that the Rp-oligomer containing four kinds of nucleobases formed a more stable duplex sequence compared with the naturally occurring type RNA. On the other hand, Tm value of the duplex sequence formed with All-(Sp)-(CpsApsGpsU)₃ dodecamer was 50.94° C., and was lower than that of the duplex sequence formed with the naturally occurring type RNA by 10.71° C., and it was found that it destabilized the duplex sequence. Further, Tm value of the duplex sequence of the non-stereocontrolled phosphorothioate RNA was 57.48° C., and thus it had a duplex sequence-forming ability almost in the middle of those of the Rp-oligomer and the Sp-oligomer, although the RNA was slightly unstable compared with the naturally occurring type RNA. The duplex sequence-forming abilities of the phosphorothioate RNAs of the various absolute configurations described above are summarized as follows.

Stability of Duplex Sequence
All-(Rp)-PS-RNA>Naturally occurring type RNA>Random PS-RNA>All-(Sp)-PS-RNA Example 12

Synthesis of Phosphorothioate RNA Dodecamer by Means of an Automatic Solid Phase Nucleic Acid Synthesizer Stereocontrolled phosphorothioate RNA oligomers were synthesized by means of an automatic solid phase synthesizer using oxazaphospholidine monomer units. Contemplating application of stereoselectively synthesized phosphorothioate RNAs to RNAi medicaments, it is very important to establish a simple and highly reproducible process that can attain large scale production of RNA oligomers by means of an automatic solid phase synthesizer. From this viewpoint, the phosphorothioate RNA dodecamers containing four kinds of nucleobases, which were prepared by manual solid phase synthesis in the previous investigation, were synthesized by using an automatic solid phase synthesizer. As the automatic solid phase synthesizer, Expedite 8909 Nucleic Acid Synthesis System produced by Applied Biosystems was used.

TABLE 10

| /* | | | Amount Time (sec) | | |
|---|---|---|---|---|---|
| /* Function | Mode | /Arg1 | /Arg2 | Description | |
| $Deblocking | | | | | |
| 144 /*Index Fract. Coll. | */ NA | 1 | 0 | "Event out ON" | |
| 0 /*Default | */ WAIT | 0 | 1.5 | "Wait" | |
| 141 /*Trityl Mon. On/Off | */ NA | 1 | 1 | "START data collection" | |
| 16 /*Dblk | */ PULSE | 10 | 0 | "Dblk to column" | |
| 16 /*Dblk | */ PULSE | 50 | 49 | "Deblock" | |
| 38 /*Diverted Wsh A | */ PULSE | 40 | 0 | "Flush system with Wsh A" | |
| 141 /*Trityl Mon. On/Off | */ NA | 0 | 1 | "STOP data collection" | |
| 38 /*Diverted Wsh A | */ PULSE | 40 | 0 | "Flush system with Wsh A" | |
| 144 /*Index Fract. Coll. | */ NA | 2 | 0 | "Event out OFF" | |
| $Coupling | | | | | |
| 1 /*Wsh | */ PULSE | 5 | 0 | "Flush system with Wsh" | |
| 2 /*Act | */ PULSE | 5 | 0 | "Flush system with Act" | |
| 18 /*A + Act | */ PULSE | 5 | 0 | "Monomer + Act to column" | |
| 2 /*Act | */ PULSE | 1 | 0 | "Chase with Act" | |
| 2 /*Act | */ PULSE | 4 | 600 | "Coupling (Total 15 min)" | |
| 1 /*Wsh | */ PULSE | 2 | 300 | "Couple monomer" | |
| 1 /*Wsh | */ PULSE | 14 | 0 | "Flush system with Wsh" | |
| $Capping | | | | | |
| 12 /*Wsh A | */ PULSE | 20 | 0 | "Flush system with Wsh A" | |
| 13 /*Caps | */ PULSE | 8 | 0 | "Caps to column" | |
| 12 /*Wsh A | */ PULSE | 6 | 30 | "Cap" | |
| 12 /*Wsh A | */ PULSE | 14 | 0 | "Flush system with Wsh A" | |
| $Oxidizing | | | | | |
| 17 /*Aux | */ PULSE | 30 | 0 | "SOx to column" | |
| 12 /*Wsh A | */ PULSE | 6 | 360 | "Slow pulse (6 min)" | |
| 12 /*Wsh A | */ PULSE | 30 | 0 | "End of cycle wash" | |

[Formula 15]

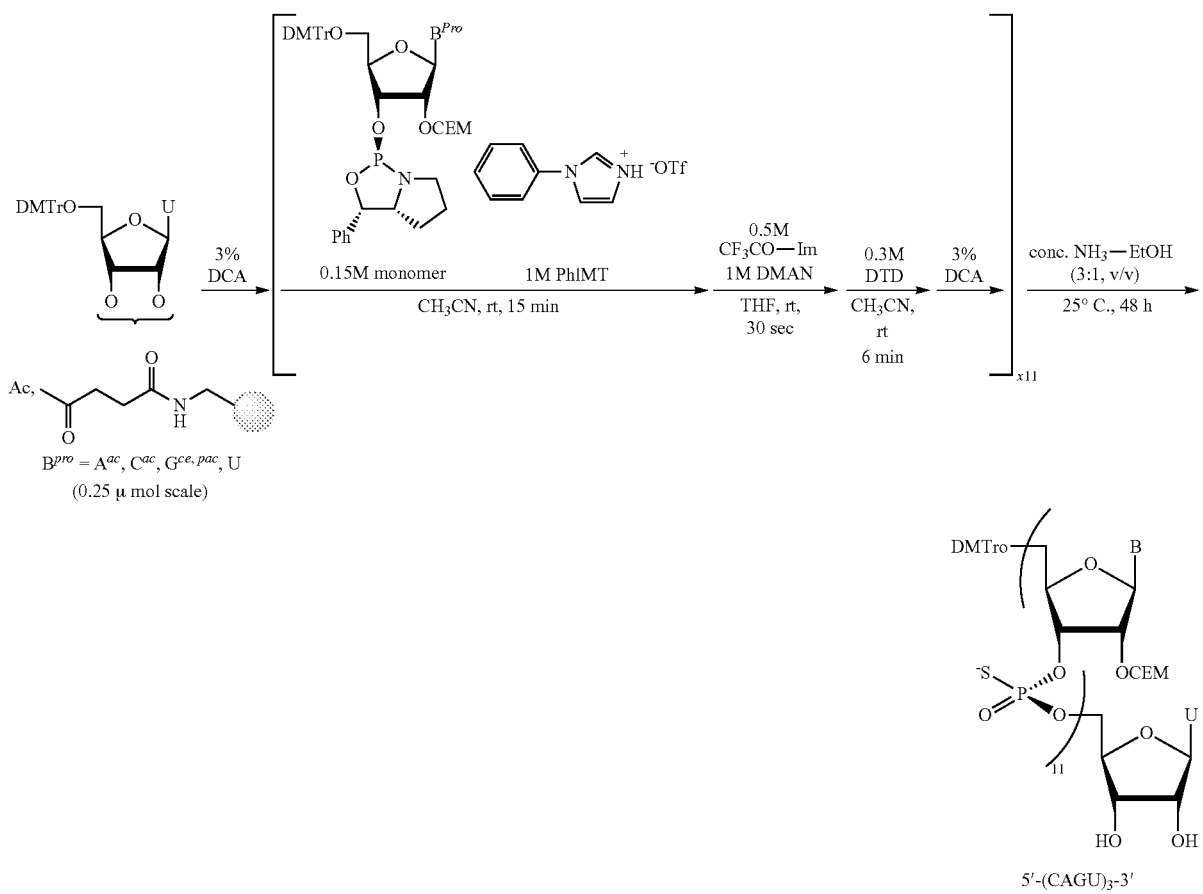

$B^{pro} = A^{ac}, C^{ac}, G^{ce,pac}, U$ (0.25 μ mol scale)

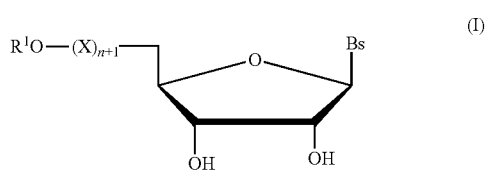

5'-(CAGU)₃-3'

Figure 6:
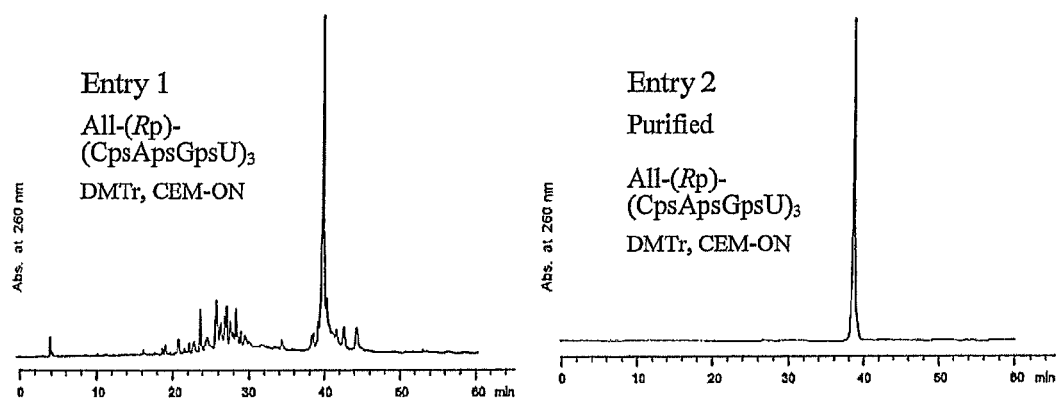
FIG. 6 shows the HPLC profiles of the phosphorothioate RNA dodecamers obtained in Example 12.

In the automatic solid phase synthesis, 5'-O-(DMTr)uridine (0.25 μmol) carried on HCP via a succinyl linker was used. The condensation time was 15 minutes. Chain length was extended by repeating the steps. Then, concentrated ammonia/EtOH (3:1, v/v, 4 ml) was added to the column, in a state that the DMTr group was remained uncleaved, for cleavage of the oligomer from the solid phase carrier at 25° C. for 4 hours, and the oligomer was transferred to a 15-ml Falcon tube by washing treatment with concentrated ammonia/EtOH (3:1, v/v, 5 ml), and left at 25° C. for 44 hours. Then, after the ammonia as the solvent was evaporated so that the volume of the solution became about 2 ml, the solution was analyzed by RP-HPLC (Senshu-Pak C18 or Waters C18, Condition D for dodecamer). As a result, each objective substance was successfully obtained in the main peak, and it was found that the condensation reaction advanced with favorable condensing efficiency in each step without any problem when the automatic solid phase synthesizer was used. Then, the oligomer was separated and purified by RP-HPLC, and the residue was desalted by lyophilization with sterilized water repeated three times. The HPLC profiles of the resulting dodecamers are shown in FIG. 6.

INDUSTRIAL APPLICABILITY

According to the method of the present invention, oligoribonucleoside phosphorothioates can be stereoselectively and efficiently synthesized. According to the method of the present invention, extremely high condensing efficiency can be stereoselectively attained, and therefore, by applying the method to the solid phase procedure, the method can attain preparation of long chain oligoribonucleoside phosphorothioates in a high yield.

What is claimed is:

1. A method for preparing a ribonucleoside phosphorothioate represented by the following formula (I) or a salt thereof:

$$R^1O-(X)_{n+1}\diagup\hspace{-1em}\underset{OH\ \ OH}{\diagdown}Bs \qquad (I)$$

wherein, $R^1$ represents hydrogen atom or a protective group of hydroxyl group, Bs represents a nucleobase which may have a protective group, n represents 0 or an integer of 1 or larger, and n of X independently represents a divalent group represented by the following formula (II-Sp) or (II-Rp):

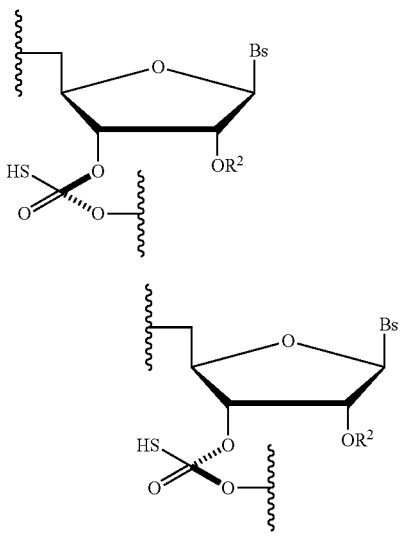

wherein, $R^2$ represents hydrogen atom or cyanoethoxymethyl group, which comprises the step of condensing a compound represented by the following formula (III):

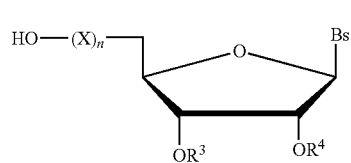

wherein, $R^3$ and $R^4$ independently represent a protective group of hydroxyl group, and one of $R^3$ and $R^4$ may represent a solid phase carrier bound via a linker as required, with an oxazaphospholidine ribonucleoside represented by the following formula (IVa) or (IVb):

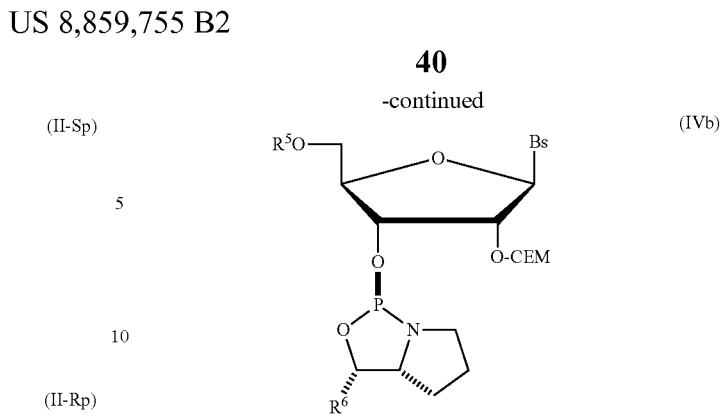

wherein, CEM represents cyanoethoxymethyl group, $R^5$ represents a protective group of hydroxyl group, and $R^6$ represents an aryl group which may have a substituent, and then sulfurizing the resulting product.

2. The method according to claim 1, wherein $R^6$ is a phenyl group.

3. The method according to claim 1, wherein $R^5$ is a 4,4'-dimethoxytrityl group.

4. The method according to claim 1, wherein the condensation is performed in the presence of an activator.

5. The method according to claim 4, wherein N-(cyanomethyl)pyrrolidinium triflate or N-phenylimidazolium triflate is used as the activator.

6. The method according to claim 1, wherein dimethyl thiuram disulfide is used as a sulfurizing agent.

7. The method according to claim 1, which comprises the step of repeating the aforementioned step n+1 times using a compound represented by the formula (III) in which n is 0 as a starting material.

8. The method according to claim 1, wherein the reaction is performed by the solid phase method.

9. The method according to claim 8, wherein a compound represented by the formula (III), in which n is 0 and which is bound to a solid phase carrier optionally via a linker, is used.

10. The method according to claim 1, wherein all of n+1 of X are divalent groups represented by the formula (II-Sp), or all of them are divalent groups represented by the formula (II-Rp).

11. A ribonucleoside phosphorothioate represented by the formula (I) mentioned in claim 1, wherein, $R^1$, Bs, n, and X have the same meanings as those defined above, and $R^2$ represents a cyanoethoxymethyl group, or a salt thereof.

12. An oxazaphospholidine ribonucleoside represented by the general formula (IVa) or (IVb) mentioned in claim 1.

* * * * *